United States Patent
Sheng et al.

(10) Patent No.: US 11,236,073 B2
(45) Date of Patent: Feb. 1, 2022

(54) ODM-201 CRYSTALLINE FORM, PREPARATION METHOD THEREFOR, AND PHARMACEUTICAL COMPOSITION THEREOF

(71) Applicant: Hangzhou SoliPharma Co., Ltd., Zhejiang (CN)

(72) Inventors: Xiaohong Sheng, Zhejiang (CN); Xiaoxia Sheng, Zhejiang (CN)

(73) Assignee: Hangzhou Solipharma Co., Ltd., Zhejiang (CN)

( * ) Notice: Subject to any disclaimer, the term of this patent is extended or adjusted under 35 U.S.C. 154(b) by 45 days.

(21) Appl. No.: 16/637,465

(22) PCT Filed: Aug. 9, 2017

(86) PCT No.: PCT/CN2017/096547
§ 371 (c)(1),
(2) Date: Feb. 7, 2020

(87) PCT Pub. No.: WO2019/028689
PCT Pub. Date: Feb. 14, 2019

(65) Prior Publication Data
US 2020/0216422 A1    Jul. 9, 2020

(51) Int. Cl.
C07D 403/12    (2006.01)
A61K 9/00    (2006.01)

(52) U.S. Cl.
CPC .......... *C07D 403/12* (2013.01); *A61K 9/0053* (2013.01); *C07B 2200/13* (2013.01)

(58) Field of Classification Search
CPC .................................................. C07D 403/12
See application file for complete search history.

(56) References Cited

U.S. PATENT DOCUMENTS

| 8,921,378 | B2 | 12/2014 | Tormakangas |
| 2019/0100536 | A1 | 4/2019 | Whlfahrt |

FOREIGN PATENT DOCUMENTS

| CN | 103492372 B | 9/2015 |
| CN | 102596910 B | 11/2015 |
| EP | 3495352 A1 | 6/2019 |
| WO | WO-2016120530 A1 | 8/2016 |
| WO | WO-2018036558 A1 | 3/2018 |
| WO | WO-2019028689 A1 | 2/2019 |

OTHER PUBLICATIONS

Prostate cancer [online] retrieved from the internet on May 21, 2021 URL: https://www.mayoclinic.org/diseases-conditions/prostate-cancer/symptoms-causes/syc-203.*
Prostate cancer prevention [online] retrieved from the internet on May 21, 2021 URL https://www.mayoclinic.org/diseases-conditions/prostate-cancer/in-depth/prostate cancer-prevention/art-20045641.*
International Search Report and Written Opinion in International Application No. PCT/CN2017/096547, State Intellectual Property Office of the P.R. China, China, dated May 10, 2018, 9 pages.

* cited by examiner

*Primary Examiner* — Shawquia Jackson
(74) *Attorney, Agent, or Firm* — Sterne, Kessler, Goldstein & Fox P.L.L.C.

(57) ABSTRACT

The present invention relates to a crystalline form of N-((s)-1-(3-(3-chloro-4-cyanophenyl)-1H-pyrazol-1-yl)prop-2-yl)-5-(1-hydroxylethyl)-1H-pyrazole-3-carboxamide (namely, ODM-201). The ODM-201 crystalline form of the present invention has one or more improved properties compared to known ODM-201. The present invention further relates to a method for preparing the ODM-201 crystalline form, a pharmaceutical composition thereof, and a use thereof in the preparation of a medicament for the treatment of nuclear receptor, specifically steroid receptor, and more specifically androgen receptor (AR)-dependent diseases and conditions.

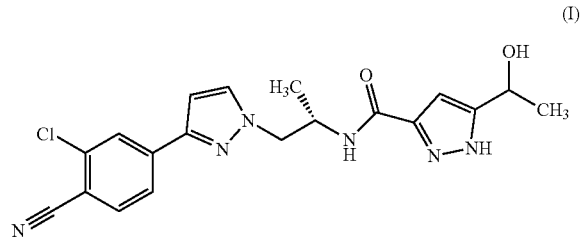

20 Claims, 10 Drawing Sheets

ODM-201 CRYSTALLINE FORM, PREPARATION METHOD THEREFOR, AND PHARMACEUTICAL COMPOSITION THEREOF

FIELD OF THE INVENTION

The present invention relates to the technical field of crystallization in pharmaceutical chemistry. Specifically, the present application relates to novel crystalline forms of ODM-201, and their preparation methods, pharmaceutical compositions and uses thereof.

BACKGROUND

ODM-201, also named as Darolutamide, is an androgen receptor (AR) antagonist that can be used to treat prostate cancer and other AR-dependent diseases and symptoms that require AR antagonism. The chemical name of ODM-201 is N—((S)-1-(3-(3-chloro-4-cyano phenyl)-1H-pyrazol-1-yl)prop-2-yl)-5-(1-hydroxyethyl)-1H-pyrazole-3-carboxamide, and its chemical structure is shown in the following formula:

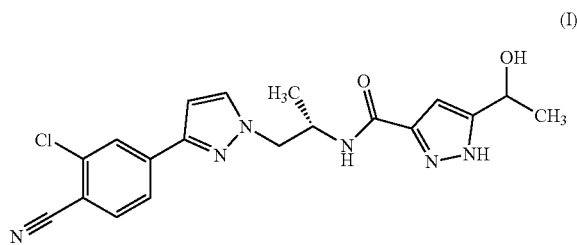 [SMILES: CC(O)c1cc(C(=O)N[C@@H](C)Cn2ccc(-c3ccc(C#N)c(Cl)c3)n2)n[nH]1]

(I)

Patent documents CN102596910(B) and CN103492372 (B) disclose the synthetic preparation method of ODM-201, and disclose the $^1$H-NMR detection data of ODM-201. The present inventors' research find that the ODM-201 obtained according to the preparation methods of Example 56 in CN102596910(B) and Example 38(f) in CN103492372 (B) are all pale yellow solids and amorphous. Amorphous form has disadvantages of being susceptible to moisture absorption, poor flowability/poor stability, etc., which could directly and negatively affect its manufacture process and the bioavailability, efficacy and shelf life of its pharmaceutical products.

Therefore, there is a need to develop ODM-201 crystalline forms with more improved properties to meet the strict requirements on the active ingredients in pharmaceutical formulations.

SUMMARY OF THE INVENTION

In view of the defects of the prior art, the purpose of the present invention is to provide crystalline forms of ODM-201, and their preparation methods, pharmaceutical compositions and uses thereof. The crystalline forms are stable crystalline solids and have one or more improved properties, especially in terms of water solubility and chemical stability. In addition, the invention also relates to preparation methods of the crystalline forms, pharmaceutical compositions containing the crystalline forms and uses thereof.

According to the purpose of the present invention, one aspect of the invention is to provide solid crystalline ODM-201 Form 1 and the preparation methods thereof.

The X-ray powder diffraction pattern of ODM-201 Form 1 in the present invention, measured using Cu-Kα radiation, has the following characteristic peaks at 2θ values: 8.4°±0.2°, 10.4°±0.2°, 14.9°±0.2° and 16.6°±0.2°.

In a preferred aspect of the present invention, the X-ray powder diffraction pattern of ODM-201 Form 1 has the following characteristic peaks at 2θ values: 9.4°±0.2°, 16.9°±0.2°, 19.10°±0.2° and 21.7°±0.2°.

In a further preferred aspect of the present invention, the X-ray powder diffraction pattern of ODM-201 Form 1 has the following characteristic peaks at 2θ values: 12.7°±0.2°, 13.5°±0.2°, 24.2°±0.2° and 25.5°±0.2°.

Non-restrictively, in one typical aspect of the present invention, the XRPD pattern of ODM-201 Form 1 is shown in FIG. 3.

Non-restrictively, the DSC thermogram of ODM-201 Form 1 is shown in FIG. 4.

Non-restrictively, the TGA thermogram of ODM-201 Crystalline Form 1 is shown in FIG. 5.

Non-restrictively, the isothermal adsorption curve of ODM-201 Form 1 is shown in FIG. 6.

Compared with the known amorphous ODM-201 in the prior art, ODM-201 Form 1 in the present invention has the following beneficial properties:

1) Amorphous ODM-201 begins to show a weak crystalline state after having been stored for 7 days at high temperature 60° C., high moisture content 97% RH, and 40° C.-75% RH, respectively. The ODM-201 Form 1 keeps its form unchanged after having been stored for 7 days at high temperature 60° C., high moisture content 97% RH, and 40° C.-75% RH, indicating that ODM-201 Form 1 in the present invention shows good crystal stability.

2) The chemical purity of amorphous ODM-201 reduces by more than 1% after having been stored under dry condition at 60° C. for 7 days. The chemical purity of ODM-201 Form 1 is essentially unchanged after having been stored for 7 days, indicating that ODM-201 Form 1 in the present invention has better chemical stability.

3) ODM-201 Form 1 (which has moisture sorption of less than 0.3% between 0% RH and 80% RH) in the present invention has lower hygroscopicity than amorphous ODM-201 (which has moisture sorption of 6.4% between 0% RH and 80% RH).

The above beneficial properties show that, compared with the known amorphous ODM-201, ODM-201 Form 1 in the present invention has many advantages and is more suitable for being used as the solid form of the active ingredient in pharmaceutical formulations. The amorphous ODM-201 has the disadvantages of poor stability, poor flowability, and high hygroscopicity, which could lead to low bioavailability, poor efficacy and short shelf life of its pharmaceutical products. ODM-201 Form 1 is markedly better in terms of hygroscopicity, chemical stability and crystal stability, therefore it has better processing characteristics which are beneficial to improve the uniformity of the formulation.

The present invention provides methods of preparing ODM-201 Form 1, which comprise any one of the following preparation methods:

1) Forming a suspension of ODM-201 in a solvent and stirring for a certain time to obtain ODM-201 Form 1; preferably, the solvent is selected from the group consisting of an ether, a ketone, an ester, an alkane (including haloalkane), a $C_3$ to $C_4$ alcohol, a methanol, a toluene, an acetonitrile, water and a mixture thereof, more preferably isopropyl alcohol, methyl tert-butyl ether, ethyl acetate, n-heptane, water or a mixture thereof.

Preferably, the mass-volume ratio of ODM-201 to the solvent ranges from 1 to 50 mg:1 mL, more preferably from 5 to 50 mg:1 mL.

Preferably, the slurry is performed at 25 to 50° C.

Preferably, the duration for stirring is from 3 to 7 days.

2) Forming a solution of ODM-201 in a solvent by heating it to 50-60° C., cooling slowly, letting stand for crystallization, separating the precipitated crystals, and drying to obtain ODM-201 Form 1.

Preferably, the solvent is selected from the group consisting of a methanol, a $C_3$ to $C_4$ alcohol, an alkane, ethyl acetate, 1,4-dioxane, nitromethane, tetrahydrofuran, water and a mixture thereof; more preferably methanol, isopropanol, tetrahydrofuran, acetonitrile, water or a mixture thereof.

Preferably, the mass-volume ratio of ODM-201 to the solvent ranges from 30 to 50 mg:1 mL.

Preferably, the cooling rate ranges from 5 to 10° C./hour.

Preferably, the duration for crystallization is 3 to 15 days, and the crystallization temperature is 4° C.

According to the purpose of the present invention, the second aspect of the invention is to provide ODM-201 Form 2 and the preparation methods thereof.

The X-ray powder diffraction pattern of ODM-201 Form 2 in the present invention, measured using Cu-Kα radiation, has the following characteristic peaks at 2θ values: 9.0°±0.2°, 13.6°±0.2°, 16.3°±0.2° and 22.6°±0.2°.

In a preferred aspect of the present invention, the X-ray powder diffraction pattern of ODM-201 Form 2 has the following characteristic peaks at 2θ values: 11.9°±0.2°, 14.8°±0.2°, 18.1°±0.2° and 24.7°±0.2°.

In a further preferred aspect of the present invention, the X-ray powder diffraction pattern of ODM-201 Form 2 has the following characteristic peaks at 2θ values: 19.0°±0.2°, 20.3°±0.2°, 23.6°±0.2° and 27.9°±0.2°.

Non-restrictively, in one typical aspect of the present invention, the X-ray powder diffraction pattern of ODM-201 Form 2 is shown in FIG. 7.

Non-restrictively, the DSC thermogram of ODM-201 Form 2 is shown in FIG. 8.

Non-restrictively, the TGA thermogram of ODM-201 Form 2 is shown in FIG. 9.

Non-restrictively, the isothermal adsorption curve of ODM-201 Form 2 is shown in FIG. 10.

Compared with the known amorphous ODM-201 in the prior art, ODM-201 Form 2 of the present invention has the following beneficial properties:

1) The amorphous ODM-201 begins to show a weak crystalline state after having been stored for 7 days at high temperature 60° C., high moisture content 97% RH, and 40° C.-75% RH, respectively. The ODM-201 Form 2 keeps its form unchanged after having been stored for 7 days at high temperature 60° C., high moisture content 97% RH, and 40° C.-75% RH, respectively, indicating that ODM-201 Form 2 in the present invention has good crystal stability.

2) The chemical purity of amorphous ODM-201 reduces by more than 1% after having been stored in a desiccator at 60° C. for 7 days. The chemical purity of ODM-201 Form 2 is essentially unchanged after having been stored for 7 days, indicating that ODM-201 Form 2 in the present invention has better chemical stability.

3) ODM-201 Form 2 (which has moisture sorption of 2.5% between 0% RH and 80% RH) in the present invention has lower hygroscopicity than amorphous ODM-201 (which has moisture sorption of 6.4% between 0% RH and 80% RH).

The above advantageous properties show that: compared with the known amorphous ODM-201 in the art, ODM-201 Form 2 in the present invention has many advantages and is more suitable for being used as the solid form of the active ingredient in pharmaceutical formulations. The amorphous ODM-201 has the disadvantages of poor stability, poor flowability, and high hygroscopicity, which could lead to low bioavailability, poor efficacy and short shelf life of its pharmaceutical products. ODM-201 Form 2 is markedly better in terms of chemical stability and crystal stability, therefore it has better processing characteristics which are beneficial to improve the uniformity of the formulation.

The present invention provides methods of preparing ODM-201 Form 2, which comprise any one of the following preparation methods:

1) Forming a solution of ODM-201 in a mixed solvent, filtering, and drying the solvent by volatilization to obtain ODM-201 Form 2; preferably, the solvent is selected from the group consisting of an alcohol, tetrahydrofuran, methyl ethyl ketone, acetone, acetonitrile, dimethyl sulfoxide, water and a mixture thereof; more preferably, a mixture of acetonitrile and water, or a mixture of acetone and water.

Preferably, the mass-volume ratio of ODM-201 to the mixed solvent ranges from 1 to 50 mg:1 mL, more preferably from 1 to 5 mg:1 mL;

Preferably, the volatilization is performed at 25 to 40° C.

Preferably, the duration for volatilization is about 1 to 14 days.

2) Forming a solution of ODM-201 in a solvent, filtering, adding 1 to 10% (wt %) polymer, dissolving by ultrasonication, drying the solvent by volatilization to obtain ODM-201 Form 2.

Preferably, the solvent is selected from the group consisting of methanol, ethanol, trifluoroethanol, 1,4-dioxane, acetone, tetrahydrofuran and a mixture thereof with water, more preferably a mixture of tetrahydrofuran and water, or a mixture of ethanol and water.

Preferably, the polymer is selected from the group consisting of polyvinyl chloride, polyethylene glycol 4000, poly(allylamine hydrochloride), polyvinyl alcohol 124, and hydroxypropyl cellulose.

Preferably, the mass-volume ratio of ODM-201 to the solvent ranges from 10 to 50 mg:1 mL.

Preferably, the volatilization is performed at 40° C.

According to a purpose of the present invention, the third aspect of the invention is to provide ODM-201 Form 4 and the preparation method thereof.

The X-ray powder diffraction pattern of ODM-201 Form 4 in the present invention, measured using Cu-Kα radiation, has the following characteristic peaks at 2θ values: 7.8°±0.20, 9.2°±0.2°, 11.2°±0.2° and 14.5°±0.2°.

In a preferred aspect of the present invention, the X-ray powder diffraction pattern of ODM-201 Form 4 has the following characteristic peaks at 2θ values: 15.5°±0.2°, 16.8°±0.2°, and 22.3°±0.2°.

In a further preferred aspect of the present invention, the X-ray powder diffraction pattern of ODM-201 Form 4 has the following characteristic peaks at 2θ values: 18.4°±0.2°, 20.2°±0.2°, and 23.5°±0.2°.

Non-restrictively, in one typical aspect of the present invention, the X-ray powder diffraction pattern of ODM-201 Form 4 is shown in FIG. 12.

Non-restrictively, the DSC thermogram of ODM-201 Form 4 is shown in FIG. 13.

Non-restrictively, the TGA thermogram of ODM-201 Form 4 is shown in FIG. 14.

Non-restrictively, the isothermal adsorption curve of ODM-201 Form 4 is shown in FIG. 15.

Compared with the known amorphous ODM-201 in the prior art, ODM-201 Form 4 in the present invention has the following beneficial properties:

1) Amorphous ODM-201 begins to show a weak crystalline state after having been stored for 7 days at high temperature 60° C., high moisture content 97% RH, and 40° C.-75% RH, respectively. The ODM-201 Form 4 keeps its form unchanged after having been stored for 7 days at high temperature 60° C., high moisture content 97% RH, and 40° C.-75% RH, respectively, indicating that ODM-201 Form 4 in the present invention shows good crystal stability.

2) The chemical purity of amorphous ODM-201 reduces by more than 1% after having been stored in a desiccator at 60° C. for 7 days. The chemical purity of ODM-201 Form 4 is essentially unchanged after having been stored for 7 days, indicating that ODM-201 Form 4 in the present invention has better chemical stability.

3) ODM-201 Form 4 (which has moisture sorption of less than 0.2% between 0% RH and 80% RH) in the present invention has lower hygroscopicity than amorphous ODM-201 (which has moisture sorption of 6.4% between 0% RH and 80% RH).

The above advantageous properties show that: compared with the known amorphous ODM-201 in the art, ODM-201 Form 4 in the present invention has many advantages and is more suitable for being used as the solid form of the active ingredient in pharmaceutical formulations. The amorphous ODM-201 has the disadvantages of poor stability, poor flowability, and high hygroscopicity, which could lead to low bioavailability, poor efficacy and short shelf life of its pharmaceutical products. ODM-201 Form 4 is markedly better in terms of chemical stability and crystal stability; therefore it has better processing characteristics which are beneficial to improve the uniformity of the formulation.

The present invention provides a method of preparing ODM-201 Form 4, which comprises the following steps:

Forming a solution of ODM-201 in a mixed solvent of water and an organic solvent by heating it to 50-60° C., slowly cooling and letting stand for crystallization, then separating the precipitated crystals and drying to obtain ODM-201 Form 4.

Preferably, the organic solvent is selected from the group consisting of trifluoroethanol, a ketone, and a mixture thereof, and more preferably trifluoroethanol.

Preferably, the mass-volume ratio of ODM-201 to the mixed solvent ranges from 30 to 68 mg:1 mL.

Preferably, the cooling rate ranges from 5 to 10° C./hour.

Preferably, the duration for crystallization is from 1 to 15 days, and the crystallization temperature is 4° C.

Preferably, the drying temperature is room temperature.

Preferably, the duration for drying is from 1 to 12 hours.

According to a purpose of the present invention, the fourth aspect of the invention is to provide ODM-201 Form 5 and the preparation method thereof.

The X-ray powder diffraction pattern of ODM-201 Form 5 in the present invention, measured using Cu-Kα radiation, has the following characteristic peaks at 2θ values: 9.2°±0.20, 13.6°±0.20, 14.4°±0.20, 14.6°±0.20, 15.5°±0.20, and 16.8°±0.2°.

In a preferred aspect of the present invention, the X-ray powder diffraction pattern of ODM-201 Form 5 has the following further characteristic peaks at 2θ values: 11.5°±0.2°, 18.4°±0.20, 19.1°±0.20, 20.4°±0.20, 23.3°±0.20, 24.2°±0.20, and 25.2°±0.2°.

In a further preferred aspect of the present invention, the X-ray powder diffraction pattern of ODM-201 Form 5 has the following characteristic peaks at 2θ values: 16.10°±0.2°, 17.7°±0.20, 22.1°±0.2°, 22.5°±0.2°, and 27.4°±0.2°.

Non-restrictively, in one typical aspect of the present invention, the X-ray powder diffraction pattern of ODM-201 Form 5 is shown in FIG. 16.

Non-restrictively, the DSC thermogram of ODM-201 Form 5 is shown in FIG. 17.

Non-restrictively, the TGA thermogram of ODM-201 Form 5 is shown in FIG. 18.

Non-restrictively, the isothermal adsorption curve of ODM-201 Form 5 is shown in FIG. 19.

Compared with the known amorphous ODM-201 in the prior art, ODM-201 Form 5 in the present invention has the following beneficial properties:

1) Amorphous ODM-201 begins to show a weak crystalline state after having been stored for 7 days at high temperature 60° C., high moisture content 97% RH, and 40° C.-75% RH, respectively. The ODM-201 Form 5 keeps its form unchanged after having been stored for 7 days at high temperature 60° C., high moisture content 97% RH, and 40° C.-75% RH, respectively, indicating that ODM-201 Form 5 in the present invention shows good crystal stability.

2) The chemical purity of amorphous ODM-201 reduces by more than 1% after having been stored in a desiccator at 60° C. for 7 days. The chemical purity of ODM-201 Form 5 is essentially unchanged after having been stored for 7 days, indicating that ODM-201 Form 5 in the present invention has better chemical stability.

3) ODM-201 Form 5 (which has moisture sorption of less than 0.5% between 0% RH and 80% RH) in the present invention has lower hygroscopicity than amorphous ODM-201 (which has moisture sorption of 6.4% between 0% RH and 80% RH).

The above advantageous properties show that: compared with the known amorphous ODM-201 in the art, ODM-201 Form 5 in the present invention has many advantages and is more suitable for being used as the solid form of the active ingredient in pharmaceutical formulations. The amorphous ODM-201 has the disadvantages of poor chemical stability, poor crystal stability, and high hygroscopicity, which could lead to low bioavailability, poor efficacy and short shelf life of its pharmaceutical products. ODM-201 Form 5 is markedly better in terms of chemical stability and crystal stability, therefore it has better processing characteristics which are beneficial to improve the uniformity of the formulation.

The present invention provides a method of preparing ODM-201 Form 5, which comprises the following steps:

Forming a solution of ODM-201 in a solvent by heating it to 40-60° C., letting stand for crystallization, then separating the precipitated crystals and drying at high temperature to obtain ODM-201 Form 5.

Preferably, the solvent is a $C_3$ to $C_4$ ketone, and more preferably acetone.

Preferably, the mass-volume ratio of the compound to the solvent ranges from 5 to 50 mg:1 mL.

Preferably, the cooling rate ranges from 5 to 10° C./hour.

Preferably, the duration for crystallization is from 1 to 5 days, and the crystallization temperature is 4° C.

Preferably, the drying temperature ranges from 115 to 160° C., and preferably from 120 to 150° C.

Preferably, the duration for drying is 0.5 to 1 hour.

According to the purpose of the present invention, the fifth aspect of the invention is to provide ODM-201 Form 3 and the preparation method thereof.

The X-ray powder diffraction pattern of ODM-201 Form 3 in the present invention, measured using Cu-Kα radiation, has the following characteristic peaks at 2θ values: 9.3°±0.20, 12.1°±0.20, 14.0°±0.20, 18.6°±0.2°, 23.3°±0.2° and 24.6°±0.2°.

In a preferred aspect of the present invention, the X-ray powder diffraction pattern of ODM-201 Form 3 has the following characteristic peaks at 2θ values: 4.7°±0.2°, 13.6°±0.2°, 20.10°±0.2°, 28.10°±0.2°, 29.10°±0.2°, and 33.70±0.2°.

The present invention provides a method of preparing ODM-201 Form 3, which comprises the following steps: forming a solution of ODM-201 in acetone at room temperature, and letting stand for crystallization at low temperature to obtain ODM-201 Form 3.

Non-restrictively, in one typical aspect of the present invention, the X-ray powder diffraction pattern of ODM-201 Form 3 is shown in FIG. 11.

In the preparation methods of ODM-201 crystalline forms of the invention, the raw material "ODM-201" can be a disclosed ODM-201 compound, a crystalline form, or an amorphous form thereof, for example, but not limited to, ODM-201 prepared according to any one of the preparation methods in patent documents CN102596910(B) and CN103492372(B). These patent documents are incorporated herein by reference in their entirety.

The terms used in the present invention:

"Room temperature" refers to a temperature between 10 to 30° C.

"Stirring" is accomplished with the routine methods in the field, such as magnetic stirring, mechanical stirring, and the stirring speed ranges from 50 to 1800 r/min, preferably 300 to 900 r/min.

"Separating" is accomplished with the routine methods in the field, such as centrifugation or filtration. Preferred method is filtration under reduced pressure, generally at a pressure less than atmospheric pressure at room temperature, preferably less than 0.09 MPa.

"Drying" is accomplished with the routine methods in the field, for example, drying at normal temperature, air drying, or drying under reduced pressure. Drying instruments and methods are not limited to, but can be a fume hood, a blast oven, a spray dryer, a fluidized bed dryer, or a vacuum oven. The pressure can be reduced pressure or atmospheric pressure, preferably less than 0.09 MPa. The drying temperature is 10 to 40° C., and the duration for drying is 10 to 72 hours, preferably 2 to 24 hours, and more preferably 2 to 8 hours.

The "crystalline form" in the present invention means that the compound is confirmed by the X-ray powder diffraction pattern characterization shown and has a unique and ordered molecular arrangement or configuration within the crystal lattice. It is well known to those skilled in the art that the experimental error depends on the instrument conditions, sample preparation and sample purity. The 2θ angles of the peaks in the XRD patterns usually vary slightly depending on the differences in instruments and samples. The differences in peak angles can differ by 1°, 0.8°, 0.5°, 0.3°, 0.1°, etc., according to different instruments, different samples, etc. Generally, the tolerance is ±0.2°, so the differences in peak angles cannot be used as the sole standard. The relative intensity of peaks can vary with samples, sample preparation, and other experimental conditions, so the order of peak intensities cannot be the sole or determining factor. The influence of experimental factors such as sample height will cause the overall shift of the peak angle, which usually allows a certain shift. Therefore, those skilled in the art can understand that any crystalline form having the same or similar characteristic peaks as the X-ray powder diffraction pattern of the present invention belongs to the scope of the present invention. "Single crystal form" refers to a single crystal form as determined by X-ray powder diffraction.

The crystalline forms of the ODM-201 according to the present invention are substantially pure and single, and it is substantially free of any other crystalline form or amorphous state. "Substantially pure" in the present invention when used to refer to a new crystalline form means that this new crystalline form comprises at least 80% (by weight) of the compound present, more preferably at least 90% (by weight), and especially at least 95% (by weight), especially at least 99% (by weight).

According to a purpose of the present invention, the sixth aspect of the present invention is to provide a pharmaceutical composition. The pharmaceutical composition contains a therapeutically effective amount of a pharmaceutically active ingredient selected from the ODM-201 crystalline forms of the present invention or the ODM-201 crystalline forms prepared by the preparation methods of the present invention, and at least one pharmaceutically acceptable carrier or adjuvant.

The ODM-201 crystalline forms of the present invention include Form 1, Form 2, Form 4, and Form 5. In addition, the pharmaceutical composition can also comprise other pharmaceutical acceptable salts of ODM-201, crystalline forms of ODM-201 or amorphous ODM-201 thereof. The dosage form of the compound used in the methods of the present invention can be determined by selected specific solid state of the compound, the administration route and patient condition. The compound crystalline forms of the present invention can be prepared according to generally accepted methods in the field to be suitable for one or more of the following administration routes, which include oral administration, sublingual administration, parenteral injection (including subcutaneous injection, intravenous injection, intramuscular injection, sternum injection or infusion technology), inhalation administration, nasal administration, or rectum administration, and the pharmaceutical formulation contains at least one active ingredient. The pharmaceutical composition of the invention is preferably provided in the form of a unit dosage form, each of dosage form can contain about 100-700 mg, more often can contain about 200-600 mg of the ODM-201 and its crystalline form of the present invention. Suitably, ODM-201 and its crystalline form can be chosen to be administered twice a day.

The term "patient" used in this patent refers to an animal that is the subject of treatment, observation or experiments, preferably a mammal, more preferably a human.

The term "treatment" as used in the present invention refers to one or more of the following: (1) prevention of a disease and symptom; for example, prevention a disease or symptom in a patient who is predisposed to the disease or symptom but have not yet suffered or shown the disease or symptom (2) inhibition the disease or symptom; for example, inhibition of the disease or symptom in a patient who is suffering or showing the disease or symptom; and (3) improvement of the disease or symptom; for example, improvement of the disease and/or symptom in a patient with the disease or symptom (i.e. reversal of the disease and/or symptom), such as reducing the severity of the disease.

The term "or" as used herein refers to alternatives, which can be combined if appropriate. The term "or" therefore includes the listed individual alternatives and combinations thereof, as long as the combinations are not mutually exclusive.

The term "effective dose" refers to a dose sufficient to elicit a therapeutic or preventive function. "Pharmacologically acceptable" means that the components of the pharmaceutical composition are compatible with each other and are suitable for the recipient.

The "pharmaceutical composition" or "composition" is intended to include a bulk composition and/or individual unit dosage form consisting of one or more active pharmaceutical ingredients containing ODM-201 crystalline forms of the present invention and any non-pharmaceutically active excipients. Bulk compositions and individual unit dosage form can contain a fixed amount of one or more of the above active pharmaceutical ingredients. Bulk compositions are materials that have not yet formed individual unit dosage forms. Examples of nonrestrictive unite dosage forms are oral dosage units such as tablets, pills, and their analogues. Similarly, the pharmaceutical composition of the present invention given to the subject in need is intended to include both bulk composition and individual unit dosage form mentioned above.

Generally, the composition of the present invention comprises an active ingredient, which is usually mixed with an excipient, diluted by an excipient, or enclosed within such a carrier which can be in the form of a capsule, a sachet, paper or other containers. When an excipient is used as a diluent, it can be a solid, a semi-solid, or a liquid material, which functions as an excipient, carrier, or medium of the active ingredient. Thus, the pharmaceutical composition can be in the form of tablets, pills, lozenges, powders, sachets, cachets, elixirs, suspensions, emulsions, solutions, syrups, aerosols (either in solid or in liquid medium), ointments, soft or hard capsules, gels, suppositories, sterile injectable solutions, and sterile packaged powders.

Examples of excipients for solid dosage form suitable for oral administration include sugars, such as lactose, glucose, sucrose, sorbitol, and mannitol, starch, Arabic gum, calcium phosphate, alginate, gelatin, calcium silicate, microcrystalline cellulose, polyvinylpyrrolidone, kaolin, cellulose, methyl cellulose, adhesives, disintegrating agents, etc. Some liquid formulations suitable for oral administration (such as suspending agents, syrups, elixirs, etc.) can use media such as water, glycol, oil or alcohol. Parenteral composition usually uses sterile water as a carrier and optionally other components such as solubilizers. Injectable solution can be prepared, for example, using a carrier containing a saline solution, a glucose solution, or a solution containing a mixture of saline and glucose. Pharmaceutical formulation can also include lubricants (such as talc powder, magnesium stearate and mineral oils), wetting agents, emulsifiers and suspensions, preservatives such as propyl hydroxybenzoate, sweeteners and flavoring agents. The compound of the present invention can be prepared by the methods known in this field, so that the active ingredient can be released rapidly, continuously or in a delayed release after drug administration.

According to the purpose of the present invention, the seventh aspect of the present invention is to provide the use of crystalline forms of ODM-201 of the present invention or ODM-201 crystalline forms prepared by using preparation methods of the present invention in the preparation of medicines for treating a disease related to androgen receptor. Especially in use for the treatment of cancer, especially AR-dependent cancers such as prostate cancer, and other diseases or symptoms that require AR antagonistic effects.

According to a purpose of the present invention, the invention provides methods for treating the diseases or symptoms related to androgen receptor; it comprises administering to a patient an effective amount of an active ingredient selected from the group consisting of ODM-201 Form 1, ODM-201 Form 2, ODM-201 Form 4, and ODM-201 Form 5 of the present invention or pharmaceutical composition comprising an active ingredient selected from the group consisting of ODM-201 Form 1, ODM-201 Form 2, ODM-201 Form 4, and ODM-201 Form 5. The diseases can be the same as those described above in the present application.

The active ingredient is usually effective in a broad dose range. For example, the daily dose of the active ingredient (either single dose or multiple doses) is generally about 0.0011-1000 mg/kg. For treatment of human adults, the preferred dose (single dose or multiple doses) is approximately 1 to 2000 mg/day. However, it should be understood that the actual amount and frequency of drug administration for any given patient vary and depend on a variety of factors, including the potency of the compound used, metabolism and duration of drug action, other compounds actually to be taken together, the disease to be treated and its severity, administration route, age, weight, excretion rate and overall response of the specific patient. Thus the above dose range shall not limit the scope of the invention in anyway. In some aspects, a dose level below the above said range can be more appropriate, while in others a larger dose without any side effects can be used, provided that the larger dose is first divided into multiple smaller doses to use throughout the day.

SPECIFIC IMPLEMENTATIONS

Figure 1:
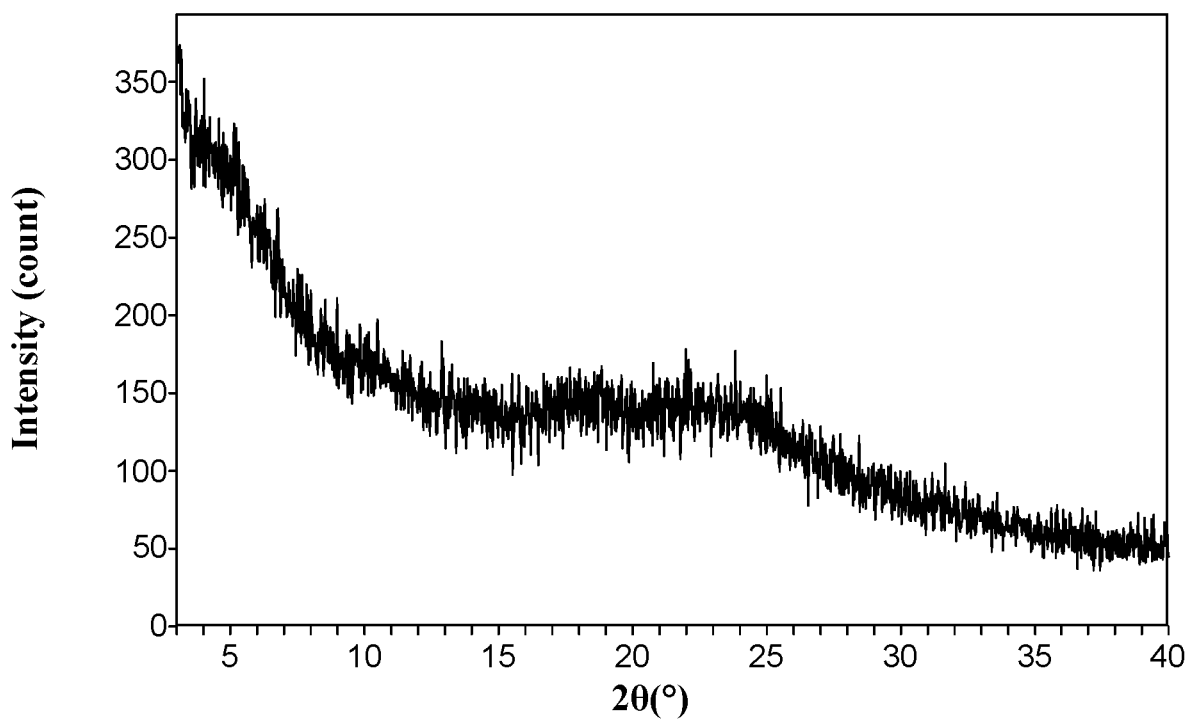
FIG. 1 is the XRPD pattern of amorphous ODM-201 prepared according to the Example 56 of CN102596910 (B).

The following examples will help to further understand the present invention, but are not intended to limit the contents of the present invention.

Instruments and characterization methods:

X-ray powder diffraction (XRPD): performed on Bruker D8 Advance diffractometer. Samples were tested at room temperature. Testing conditions: scan range 3-40° 2θ, step size 0.02°2θ, and speed 0.2 s/step.

Differential thermal analysis (DSC) data were collected on TA Instruments Q200 MDSC. Method: A sample of 1 to 10 mg was placed in a sealed aluminum pan, and the sample was heated from room temperature to 300° C. at a heating rate of 10° C./min under the protection of dry nitrogen gas purge at 40 mL/min.

Thermogravimetric analysis (TGA) data were collected on TA Instruments Q500 TGA. Method: A sample of 5 to 15 mg was placed in a platinum pan, using High Resolution TM, the sample was heated from room temperature to 350° C. at a heating rate of 10° C./min under the protection of dry nitrogen gas purge at 40 mL/min.

Dynamic vapor sorption data and isothermal sorption data were collected on TA Instruments Q5000 TGA. Method: A sample of 1 to 10 mg was placed in a platinum pan; the weight change of the sample during the change in relative humidity from 0% to 80% to 0% was measured.

$^1$H Nuclear magnetic resonance spectrum ($^1$H-NMR) data were collected on Bruker Ascend Tm 400 nuclear magnetic resonance spectrometer under the following conditions: full frequency excitation, spectral width 30 ppm, single pulse, 30° angle excitation, 16 scans, digital orthogonal detection, temperature control 298K.

HPLC purity data were collected on Ultimate 3000 high performance liquid chromatography under the following conditions: column AY-H (4.6*100 mm, 5 μm) detection wavelength 270 nm, column temperature 40° C., flow rate 0.8 mL/min, injection volume 5 μL. The sample was dissolved in ethanol to make a solution concentration about 1 mg/mL, and a gradient method using HPLC measurements to determine the purity of the sample.

|  | Time (min) | % mobile phase A | % mobile phase B |
|---|---|---|---|
| gradient | 0.00 | 99 | 1 |
|  | 15.00 (stop) | 99 | 1 |
| mobile phase A |  | ethanol |  |
| mobile phase B |  | methanol ammonia |  |

Unless particularly specified, all reagents used in the Examples were commercially available.

Unless particularly specified, all Examples were operated at room temperature.

Preparation Example 1

Preparation of Amorphous ODM-201

ODM-201 obtained by referring to the preparation method of Example 56 in patent document CN102596910 (B) is a light yellow solid.

The $^1$H-NMR (CDCl$_3$) data of the product are as follows: $^1$H-NMR (400 MHz; d$_6$-DMSO): δ 1.11 (d, 3H), 1.38 (d, 3H), 4.22-4.48 (m, 3H), 4.74-4.84 (m, 1H), 4.41 (d, 1H), 6.40 (s, 1H), 6.94 (d, 1H), 7.81 (d, 1H), 7.92-8.05 (m, 2H), 8.09 (d, 1H), 8.20 (d, 1H), 13.04 (s, 1H), indicating that it is the known compound ODM-201.

Its XRPD pattern shown in FIG. 1, indicating that it is an amorphous sample.

Figure 2:
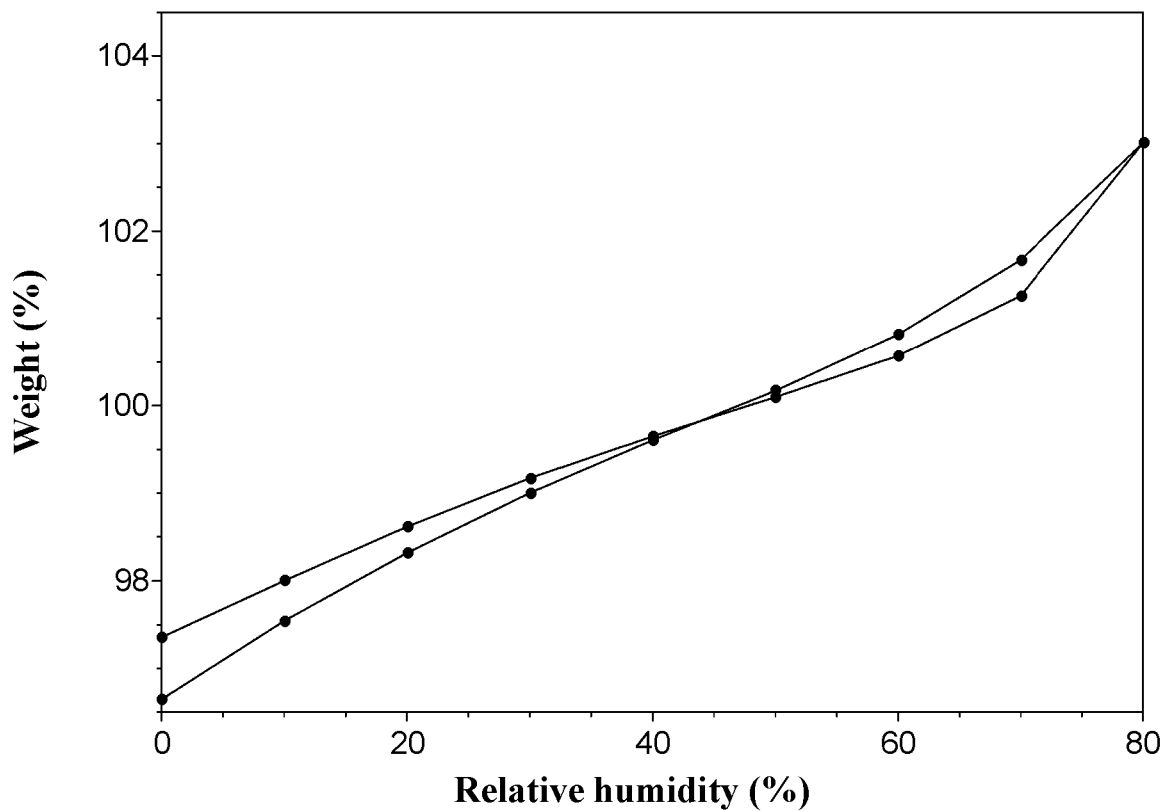
FIG. 2 is the isothermal sorption curve of amorphous ODM-201 prepared according to the Example 56 of CN102596910 (B).

Its isothermal sorption curve shown in FIG. 2, indicating that there is a weight change of 6.4% in the range of 0% RH to 80% RH.

Preparation Example 2

Preparation of Amorphous ODM-201

ODM-201 obtained by referring to the preparation method of Example 38 (f) in patent document CN103492372 (B) is a pale yellow solid.

The $^1$H-NMR (CDCl$_3$) data of the product are as follows: $^1$H-NMR (400 MHz, DMSO-d$_6$): δ 1.12 (d, 3H), 1.39 (d, 3H), 4.24-4.52 (m, 3H), 4.76-4.86 (m, 1H), 5.42 (d, 1H), 6.42 (bs, 1H), 6.94 (d, 1H), 7.82 (d, 1H), 8.00 (bs, 2H), 8.09 (bs, 1H), 8.20 (d, 1H), 13.05 (bs, 1H), indicating that it is the known compound ODM-201.

The sample prepared in Preparation Example 2 had the same or similar XRPD pattern (not shown) and isothermal adsorption curve (not shown) as the sample in Preparation Example 1, indicating that the sample in Preparation Example 2 and the sample in Preparation Example 1 have the same form.

Example 1

Water (4 mL) was added to ODM-201 (20 mg) to form a suspension, stirred at 50° C. for 5 days, and filtered to obtain ODM-201 Form 1 (18.5 mg).

Figure 3:
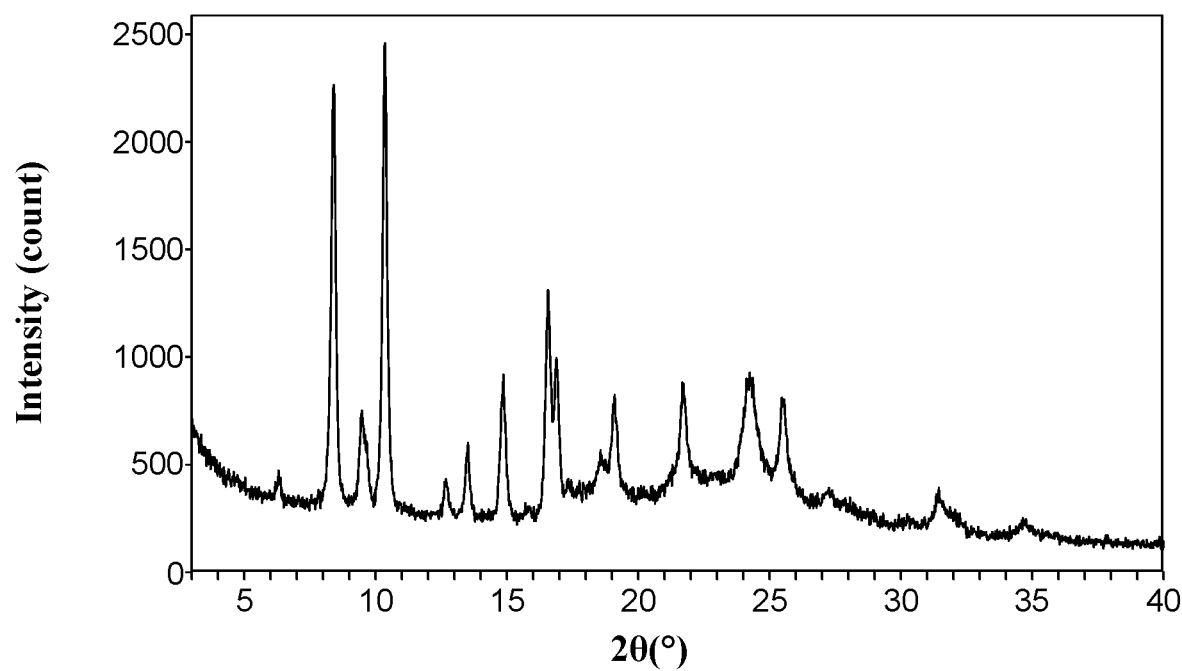
FIG. 3 is the XRPD pattern of ODM-201 Form 1 in the present invention.
Figure 4:
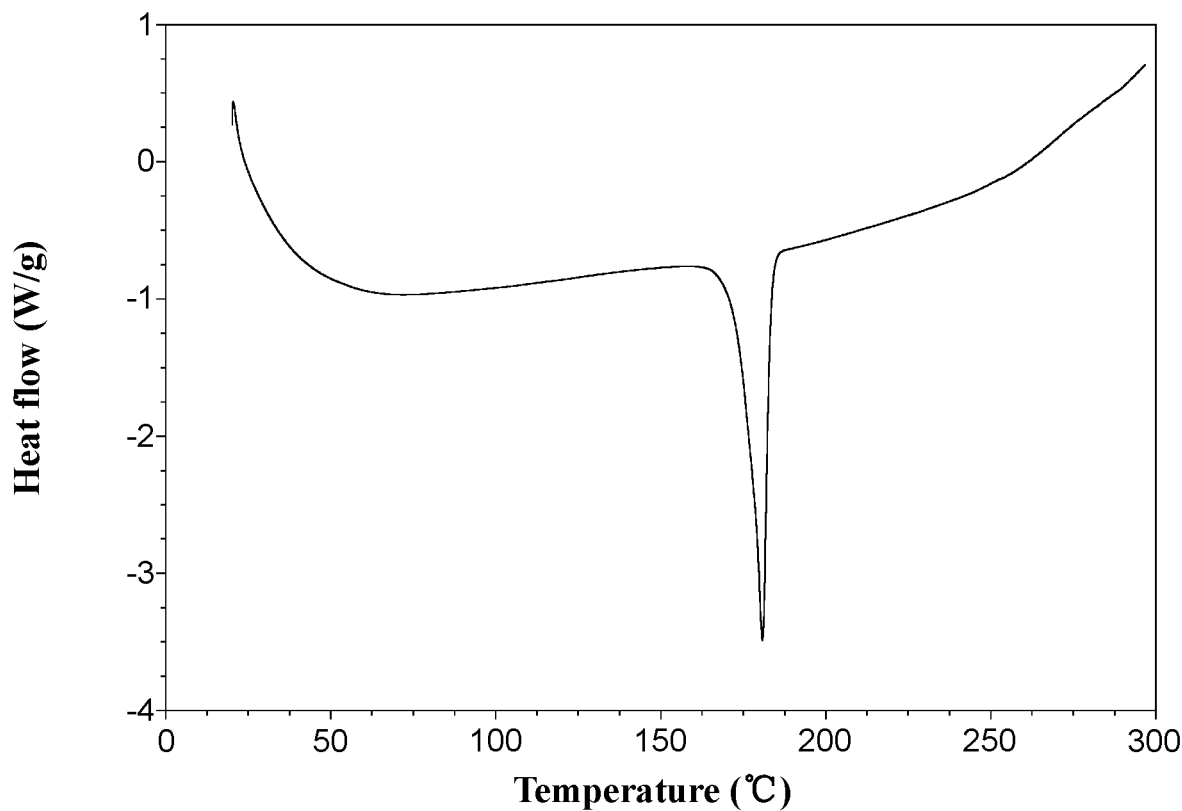
FIG. 4 is the DSC thermogram of ODM-201 Form 1 in the present invention.
Figure 5:
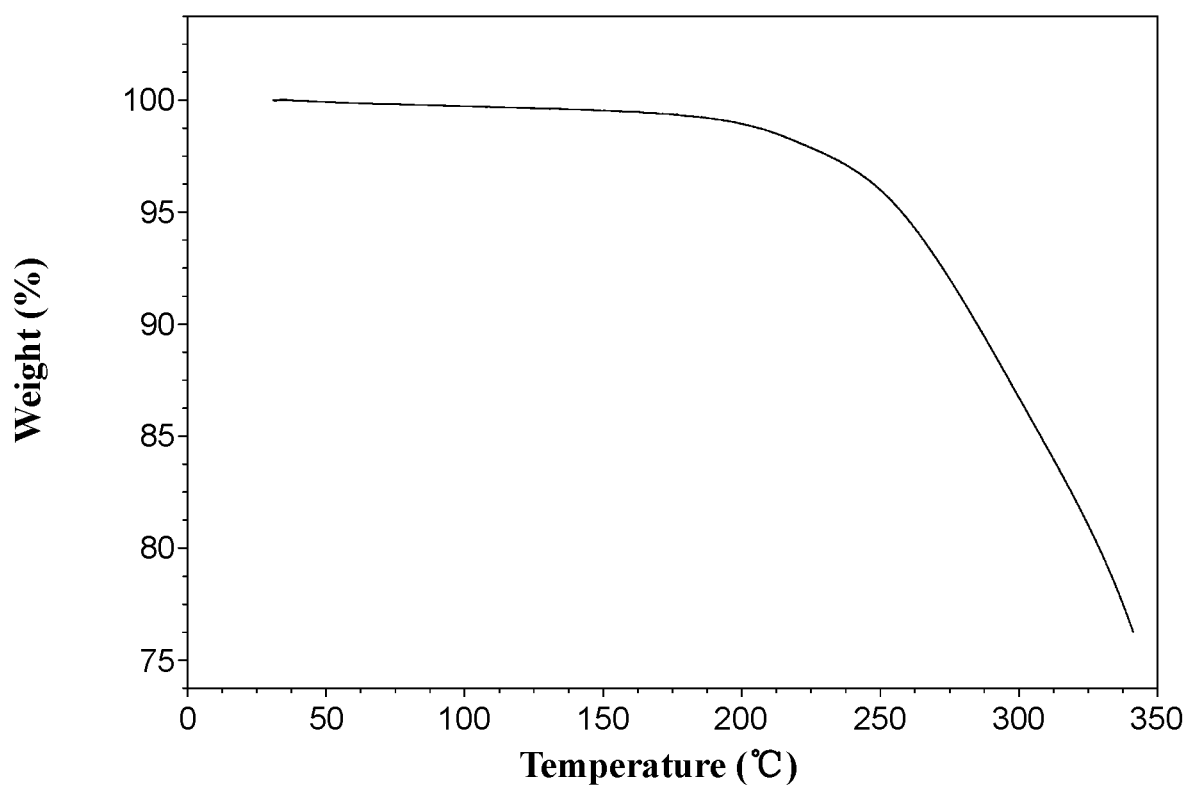
FIG. 5 is the TGA thermogram of ODM-201 Form 1 in the present invention.
Figure 6:
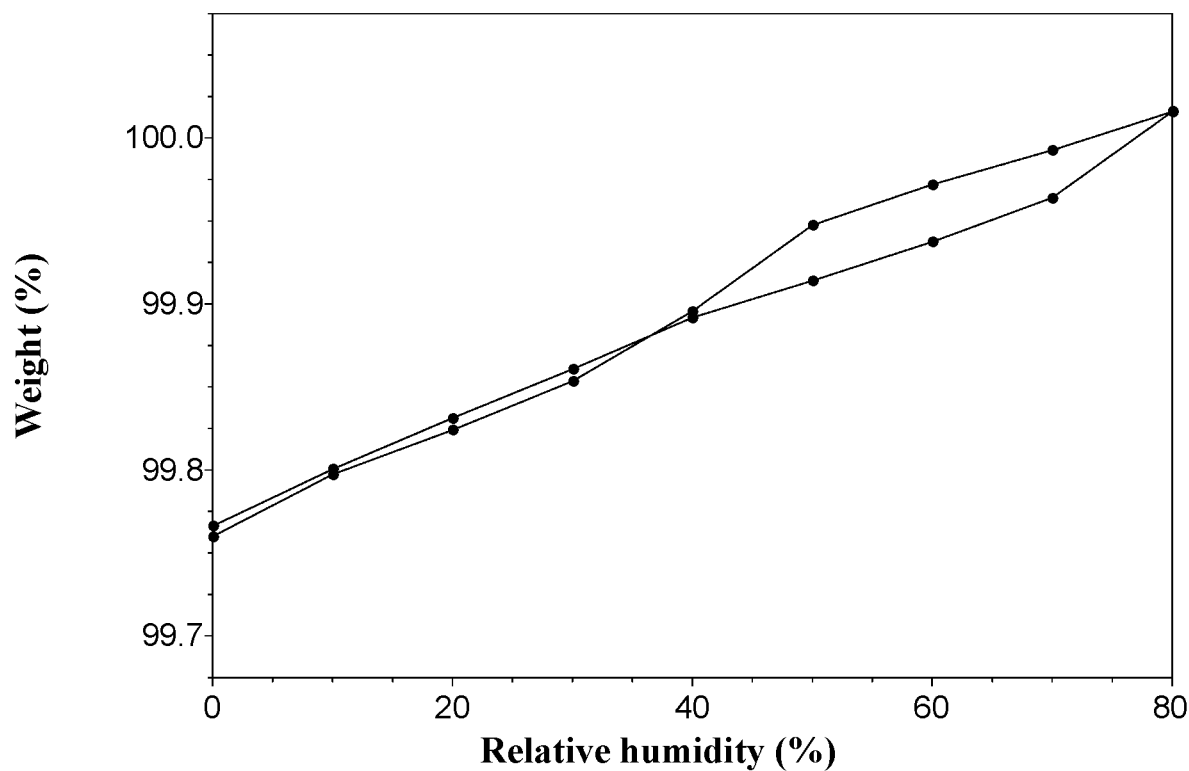
FIG. 6 is the isothermal sorption curve of ODM-201 Form 1 in the present invention.

Its XRPD pattern is shown in FIG. 3.
Its DSC thermogram is shown in FIG. 4.
Its TGA thermogram is shown in FIG. 5.
Its isothermal sorption curve is shown in FIG. 6.

Example 2

Isopropyl ether (20 mL) was added to ODM-201 (20 mg) to form a suspension, stirred at 25° C. for 7 days, and filtered to obtain ODM-201 Form 1 (17.6 mg).

Example 3

ODM-201 Form 1 can also be obtained by replacing the solvent in Example 2 with any one of the following solvents in the table below.

| Experiment Number | Solvents |
|---|---|
| Experiment 1 | methyl tert-butyl ether |
| Experiment 2 | ethyl acetate |
| Experiment 3 | sec-butanol |
| Experiment 4 | n-heptane |
| Experiment 5 | isopropanol |
| Experiment 6 | nitromethane |
| Experiment 7 | toluene |
| Experiment 8 | acetonitrile |

Example 4

Isopropanol (0.2 mL) and diethyl ether (0.2 mL) were added to ODM-201 (20 mg) to form a suspension, stirred at room temperature for 3 days, and filtered to obtain ODM-201 Form 1 (14.2 mg).

Example 5

ODM-201 Form 1 can also be obtained by replacing the solvents in Example 4 with any pair of the following solvents in the table below.

| Experiment Number | Solvent 1 | Solvent 2 |
|---|---|---|
| Experiment 1 | n-butanol | isopropyl acetate |
| Experiment 2 | acetone | cyclohexane |
| Experiment 3 | isopropyl ether | nitromethane |
| Experiment 4 | isopropanol | water |
| Experiment 5 | toluene | ethyl acetate |
| Experiment 6 | n-heptane | acetonitrile |

Example 6

Methanol (1.0 mL) was added to ODM-201 (45 mg) at 50° C. to form a solution, cooled to 4° C. at a cooling rate of 10° C./hour and let stand for crystallization for 10 days, filtered, and dried under vacuum at room temperature for 8 hours to obtain ODM-201 Form 1 (38 mg).

Example 7

Acetonitrile (0.9 mL) was added to ODM-201 (45 mg) at 50° C. to form a solution, cooled to 4° C. at a cooling rate of 10° C./hour and let stand for crystallization for 15 days, filtered, and dried under vacuum at room temperature for 12 hours to obtain ODM-201 Form 1 (35.5 mg).

Example 8

ODM-201 Form 1 can also be obtained by replacing the solvent in Example 7 with any one of the following solvents in the table below.

| Experiment Number | Solvents |
|---|---|
| Experiment 1 | nitromethane |
| Experiment 2 | n-butanol |
| Experiment 3 | ethyl acetate |
| Experiment 4 | 1,4-dioxane |
| Experiment 5 | tetrahydrofuran |
| Experiment 6 | chloroform |

Example 9

Tetrahydrofuran (0.3 mL) and water (1.2 mL) were added successively to ODM-201 (45 mg) at 60° C. to form a solution, cooled to 4° C. at a cooling rate of 5° C./hour and let stand for crystallization for 3 days, filtered, and dried under vacuum at room temperature for 1 hour to obtain ODM-201 Form 1 (36 mg).

Example 10

ODM-201 Form 1 can also be obtained by replacing the solvents in Example 9 with any pair of the following solvents in the table below.

| Experiment Number | Solvent 1 | Solvent 2 |
|---|---|---|
| Experiment 1 | methanol | water |
| Experiment 2 | isopropanol | water |
| Experiment 3 | n-propanol | water |
| Experiment 4 | acetonitrile | water |
| Experiment 5 | isopropyl acetate | tetrahydrofuran |
| Experiment 6 | ethyl acetate | n-heptane |

The samples prepared in Examples 2 to 10 had the same or similar XRPD pattern (not shown), DSC thermogram (not shown) and TGA thermogram (not shown) as the sample in Example 1, indicating that the sample in Examples 2 to 10 and the sample in Example 1 have the same crystalline form.

Example 11

Acetone (50 mL) was added to ODM-201 (50 mg) to form a solution, filtered and volatilized for crystallization at 25° C. for 5 days. After drying by volatilization, ODM-201 Form 2 was obtained.

Figure 7:
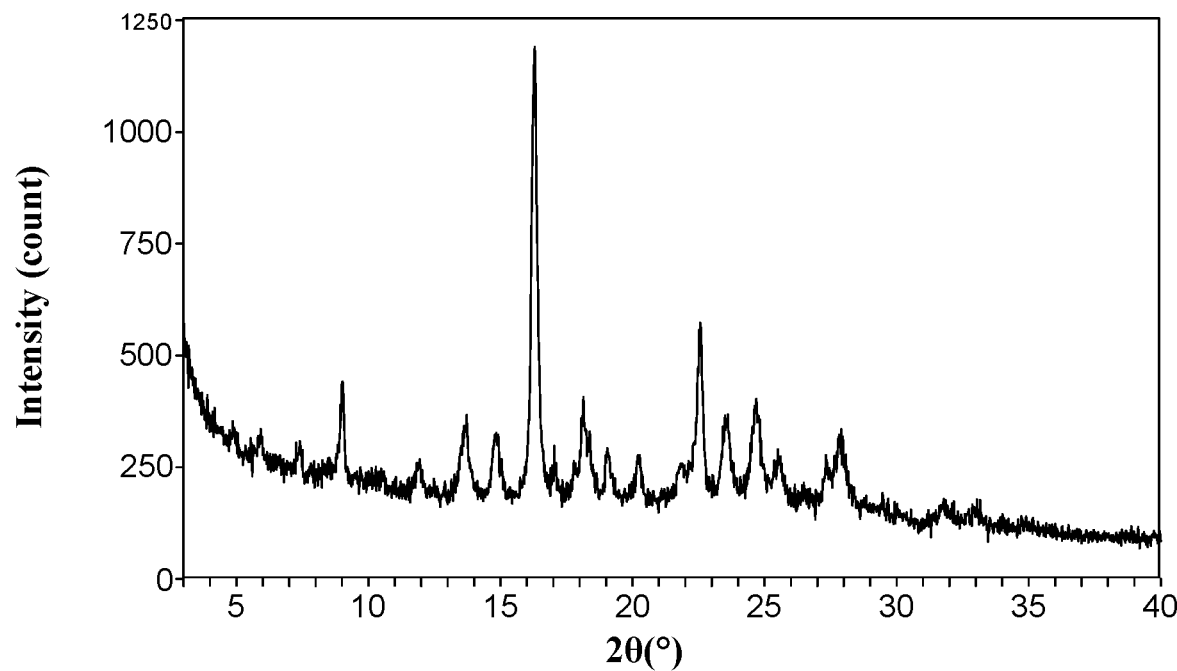
FIG. 7 is the XRPD pattern of ODM-201 Form 2 in the present invention.
Figure 8:
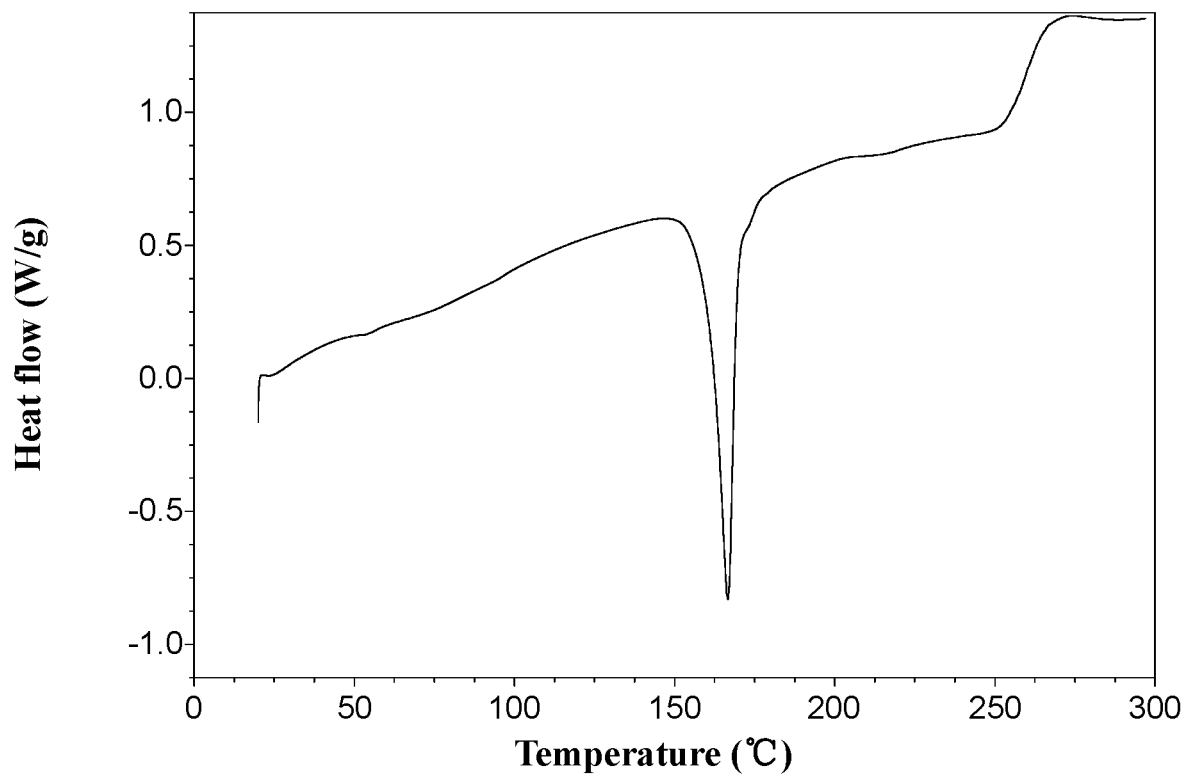
FIG. 8 is the DSC thermogram of ODM-201 Form 2 in the present invention.
Figure 9:
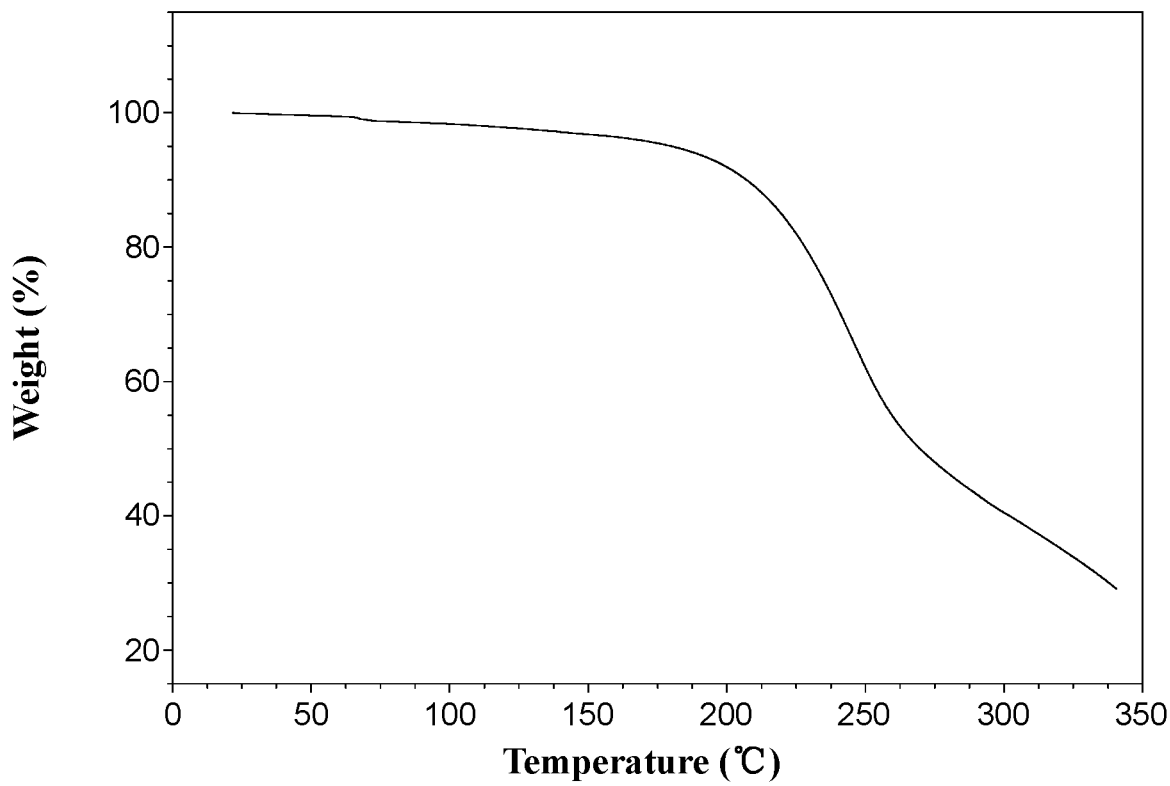
FIG. 9 is the TGA thermogram of ODM-201 Form 2 in the present invention.
Figure 10:
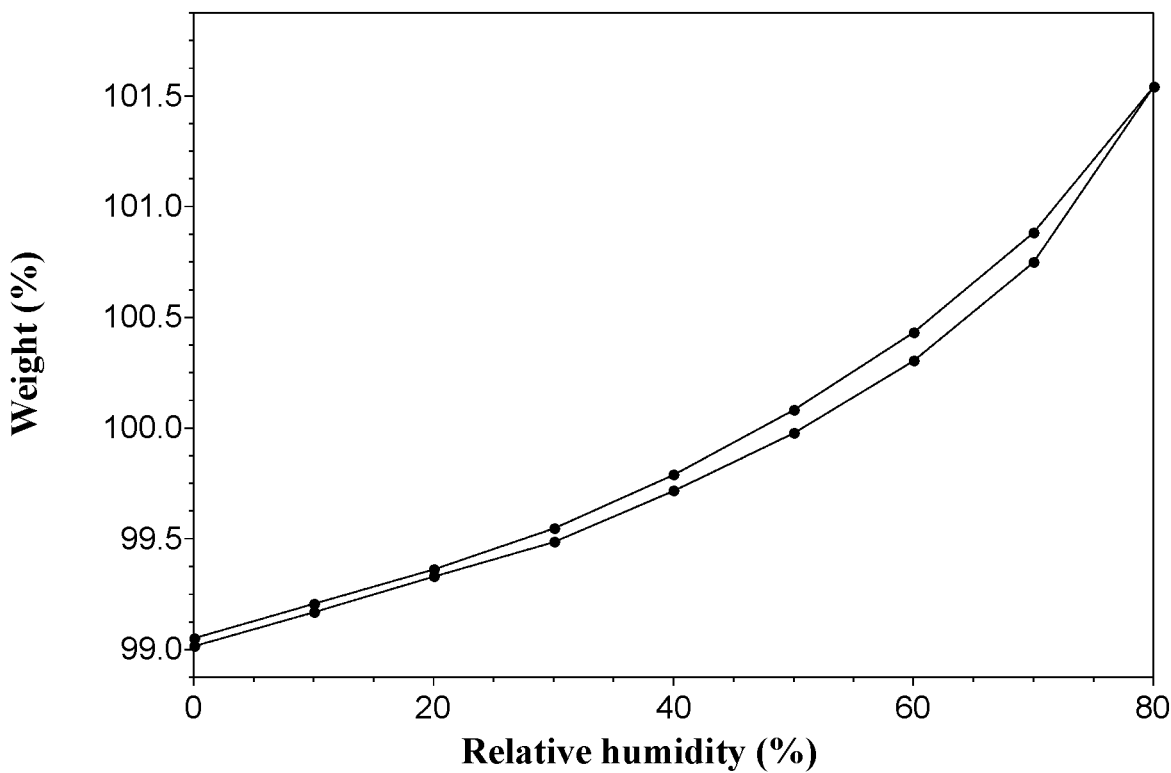
FIG. 10 is the isothermal sorption curve of ODM-201 Form 2 in the present invention.
Figure 11:
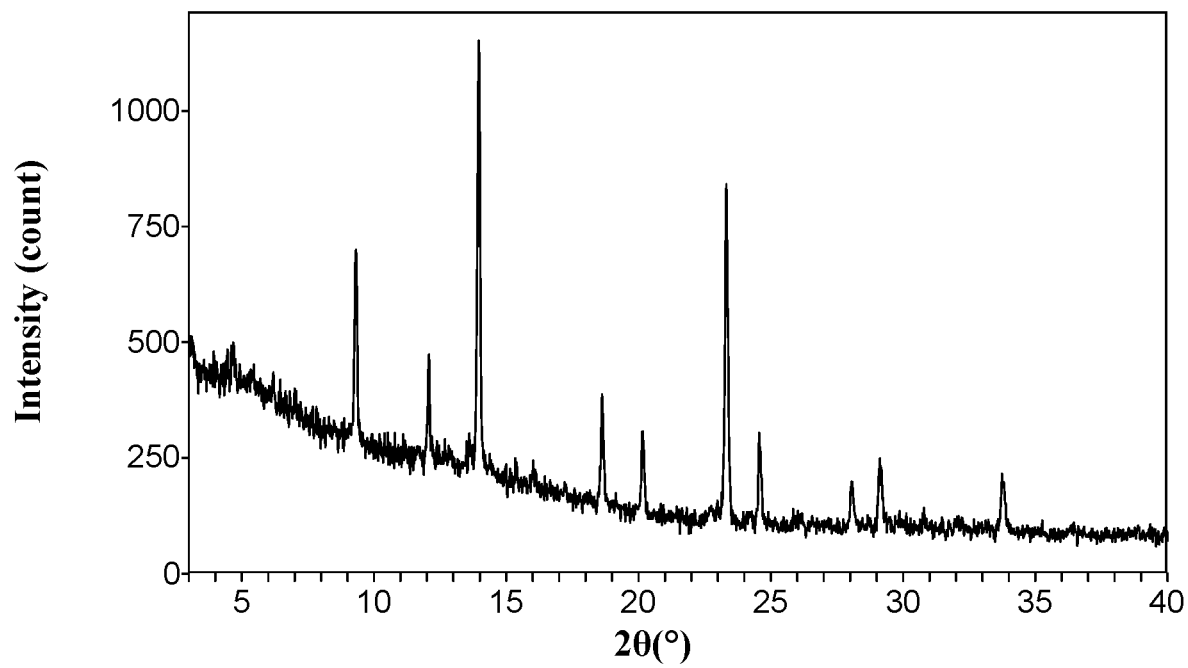
FIG. 11 is the XRPD pattern of ODM-201 Form 3 in the present invention.

Its XRPD pattern is shown in FIG. 7.
Its DSC thermogram is shown in FIG. 8.
Its TGA thermogram is shown in FIG. 9.
Its isothermal sorption curve is shown in FIG. 10.

Example 12

Tetrahydrofuran (20 mL) was added to ODM-201 (100 mg) to form a solution, filtered and volatilized for crystallization at 40° C. for 1 day. After drying by volatilization, ODM-201 Form 2 was obtained.

Example 13

Dimethyl sulfoxide (2 mL) was added to ODM-201 (100 mg) to form a solution, filtered and volatilized for crystallization at 40° C. for 10 days. After drying by volatilization ODM-201 Form 2 was obtained.

Example 14

ODM-201 Form 2 can also be obtained by replacing the solvent in Example 13 with any one of the following solvents in the table below.

| Experiment Number | Solvents |
|---|---|
| Experiment 1 | n-propanol |
| Experiment 2 | methyl ethyl ketone |
| Experiment 3 | sec-butanol |

Example 15

Acetonitrile (20 mL) and water (10 mL) were added to ODM-201 (100 mg) to form a solution, filtered and volatilized for crystallization at 25° C. for 14 days. After drying by volatilization, ODM-201 Form 2 was obtained.

Example 16

ODM-201 Form 2 can also be obtained by replacing the solvents in Example 15 with any pair of the following solvents in the table below.

| Experiment Number | Solvent 1 | Solvent 2 |
| --- | --- | --- |
| Experiment 1 | methanol | water |
| Experiment 2 | n-propanol | water |
| Experiment 3 | acetone | water |
| Experiment 4 | tetrahydrofuran | water |
| Experiment 5 | methanol | water |
| Experiment 6 | acetonitrile | tetrahydrofuran |

Example 17

Tetrahydrofuran (10 mL) was added to ODM-201 (100 mg) to form a solution, filtered, followed by addition of polyvinyl chloride (10% wt %), dissolved by ultrasonic method, and drying by volatilization at 40° C. to obtain ODM-201 Form 2.

Example 18

A mixed solvent (8 mL) of acetone and water was added to ODM-201 (100 mg) to form a solution, filtered, followed by addition of polyvinyl chloride (1% wt %), dissolved by ultrasonic method, and drying by volatilization at 40° C. to obtain ODM-201 Form 2.

Example 19

A mixed solvent (2 mL) of methanol and tetrahydrofuran was added to ODM-201 (100 mg) to form a solution, filtered, followed by addition of polyvinyl chloride (5% wt %), dissolved by ultrasonic method, and drying by volatilization at 40° C. to obtain ODM-201 Form 2.

Example 20

ODM-201 Form 2 can also be obtained by replacing the polymer in Example 19 with any one of the following polymers in the table below.

| Experiment Number | Solvents |
| --- | --- |
| Experiment 1 | polyethylene glycol 4000 |
| Experiment 2 | Poly(allylamine hydrochloride) |
| Experiment 3 | polyvinyl alcohol 124 |
| Experiment 4 | hydroxypropyl cellulose |

Example 21

ODM-201 Form 2 can also be obtained by replacing the solvents in Example 19 with any of the following solvents in the table below.

| Experiment Number | Solvent 1 | Solvent 2 |
| --- | --- | --- |
| Experiment 1 | methanol | / |
| Experiment 2 | 1,4-dioxane | / |
| Experiment 3 | trifluoroethanol | / |
| Experiment 4 | acetone | / |
| Experiment 5 | 1,4-dioxane | water |
| Experiment 6 | methanol | acetone |

The samples prepared in Examples 12 to 21 had the same or similar XRPD pattern (not shown), DSC thermogram (not shown) and TGA thermogram (not shown) as the sample in Example 11, indicating that the samples in Examples 12 to 21 and the sample in Example 11 have the same crystalline form.

Example 22

Water (0.22 mL) and trifluoroethanol (2.0 mL) were added successively to ODM-201 (150 mg) at 60° C. to form a solution, cooled to 4° C. at a cooling rate of 5° C./hour and let stand for crystallization for 1 day, filtered, and dried under vacuum at room temperature for 1 hour to obtain ODM-201 Form 4 (121 mg).

Figure 12:
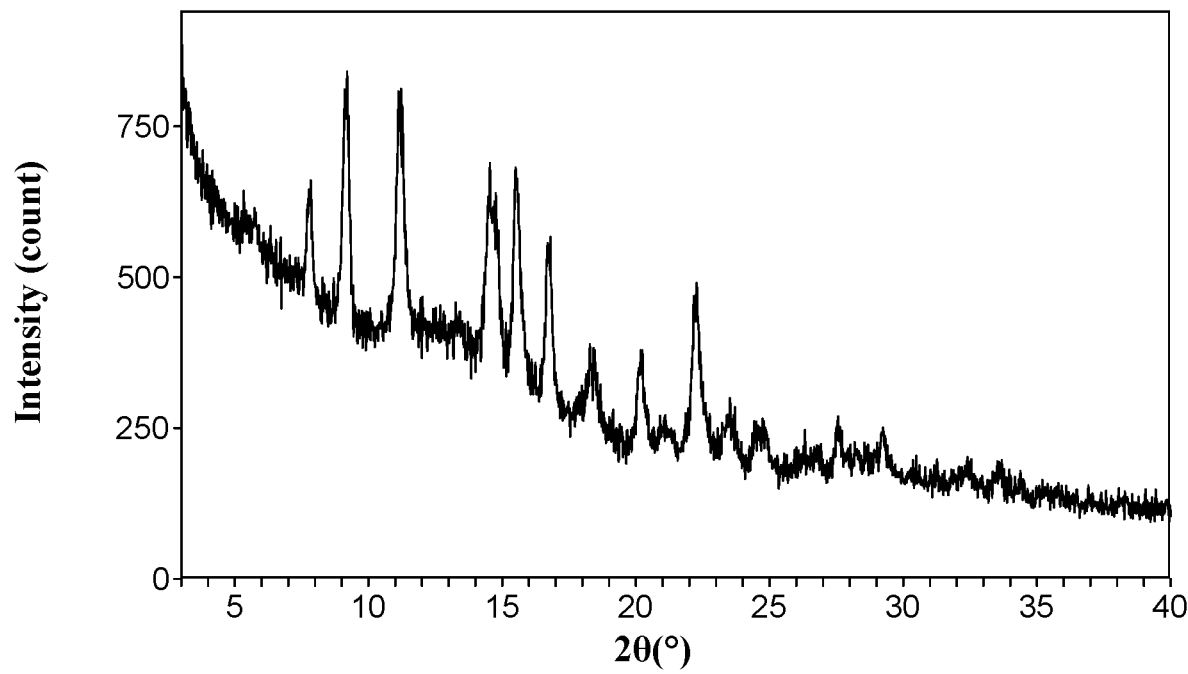
FIG. 12 is the XRPD pattern of ODM-201 Form 4 in the present invention.
Figure 13:
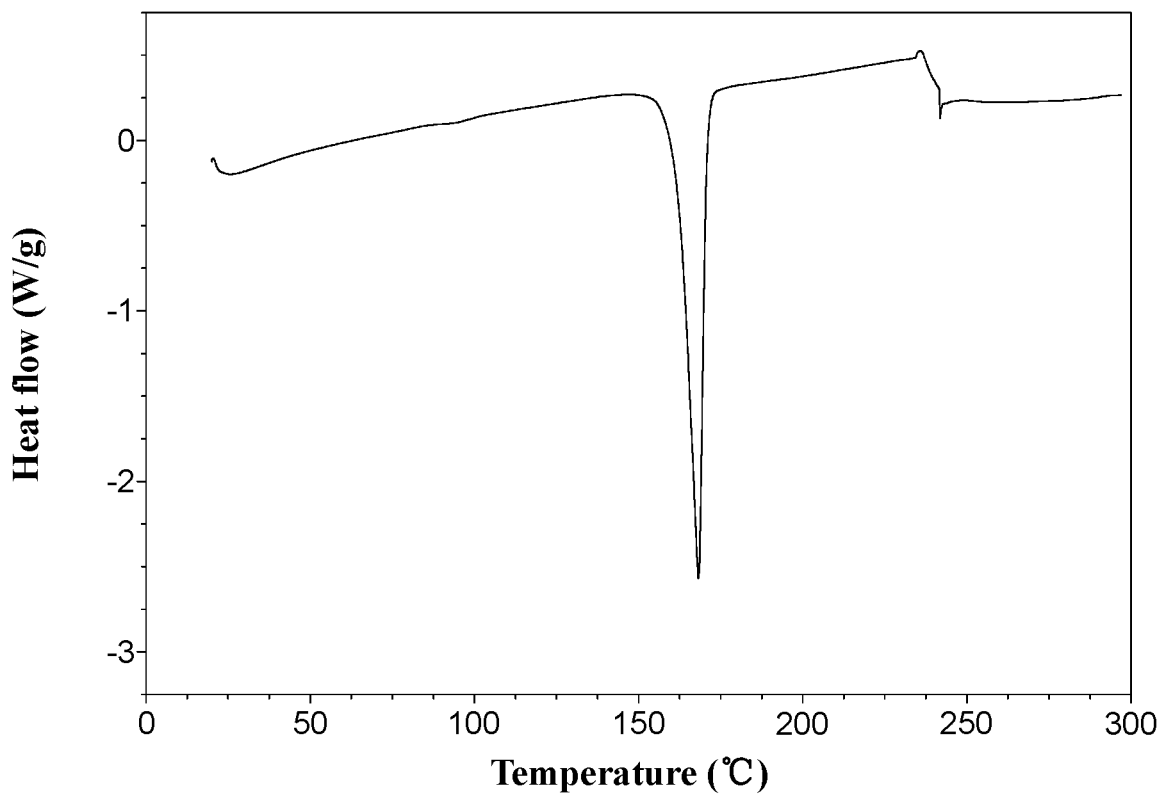
FIG. 13 is the DSC thermogram of ODM-201 Form 4 in the present invention.
Figure 14:
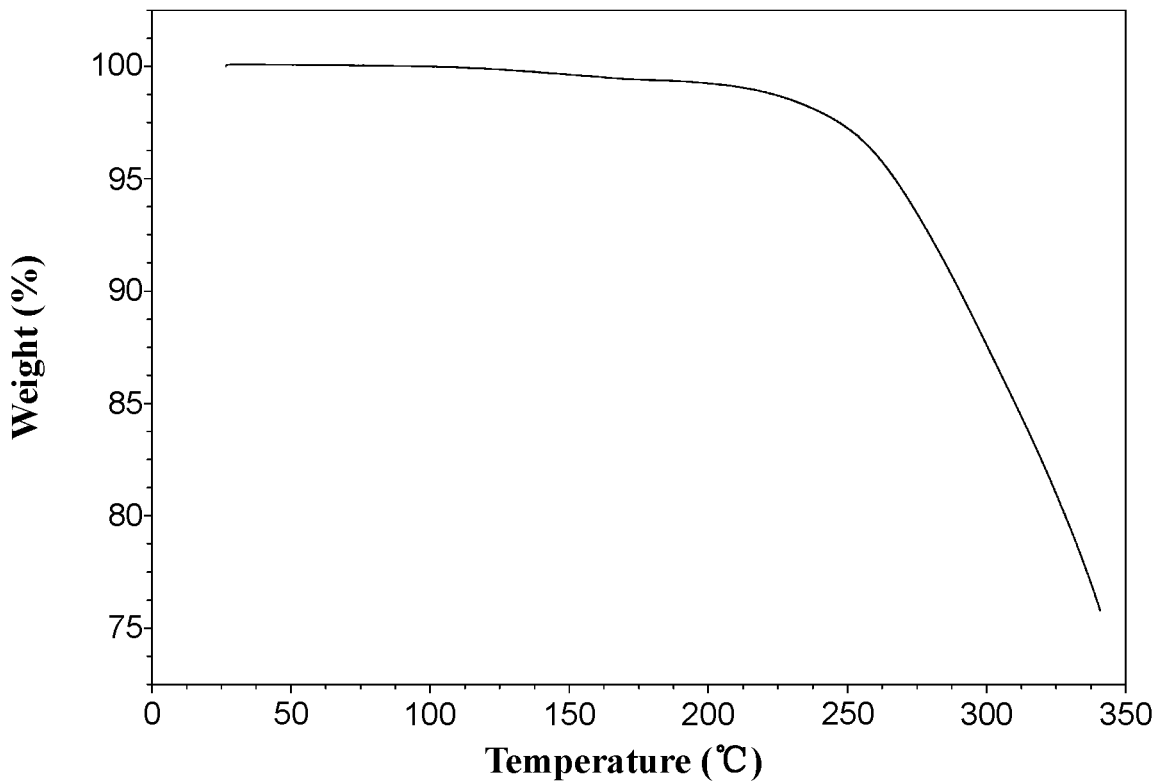
FIG. 14 is the TGA thermogram of ODM-201 Form 4 in the present invention.
Figure 15:
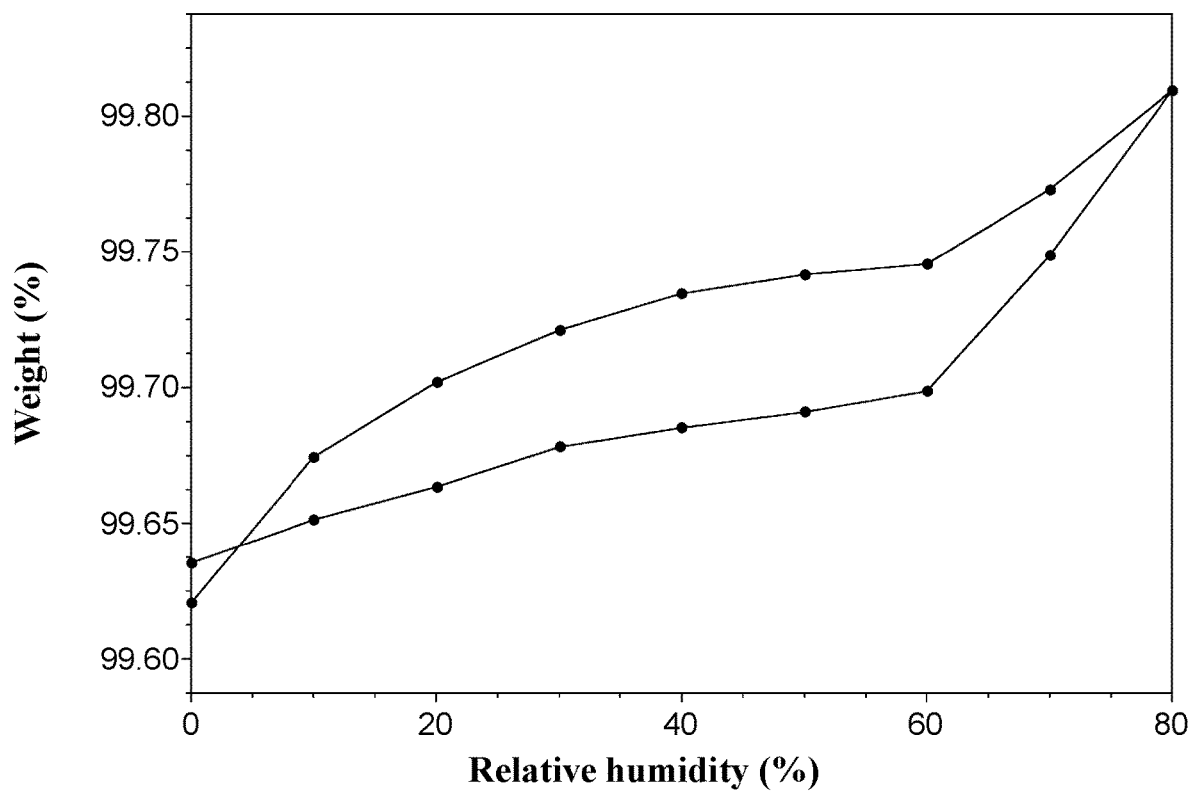
FIG. 15 is the isothermal sorption curve of ODM-201 Form 4 in the present invention.

Its XRPD pattern is shown in FIG. 12.
Its DSC thermogram is shown in FIG. 13.
Its TGA thermogram is shown in FIG. 14.
Its isothermal sorption curve is shown in FIG. 15.

Example 23

Water (3.0 mL) and acetone (2.0 mL) were added successively to ODM-201 (150 mg) at 50° C. to form a solution, cooled to 4° C. at a cooling rate of 10° C./hour and let stand for crystallization for 15 days, filtered, and dried under vacuum at room temperature for 12 hours to obtain ODM-201 Form 4 (112 mg).

Example 24

Water (1.0 mL) and trifluoroethanol (2.0 mL) were added successively to ODM-201 (150 mg) at 56° C. to form a solution, cooled to 4° C. at a cooling rate of 8° C./hour and let stand for crystallization for 10 days, filtered, and dried under vacuum at room temperature for 8 hours to obtain ODM-201 Form 4 (132 mg).

The samples prepared in Examples 23 to 24 had the same or similar XRPD pattern (not shown), DSC thermogram (not shown) and TGA thermogram (not shown) as the sample in Example 22, indicating that the samples in Examples 23 to 24 and the sample in Example 22 have the same crystalline form.

Example 25

Acetone (8.0 mL) was added to ODM-201 (150 mg) at 50° C. to form a solution, cooled to 4° C. at a cooling rate of 10° C./hour and let stand for crystallization for 1 day, filtered, and dried under vacuum at 120° C. for 0.5 hour to obtain ODM-201 Form 5 (125 mg).

Figure 16:
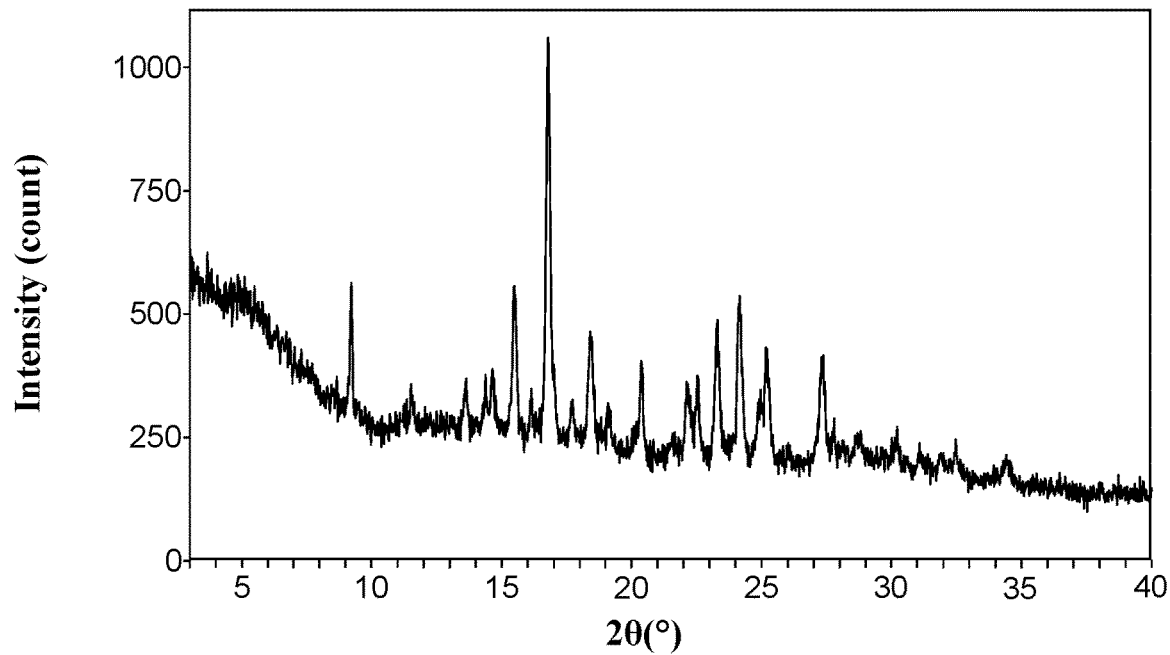
FIG. 16 is the XRPD pattern of ODM-201 Form 5 in the present invention.
Figure 17:
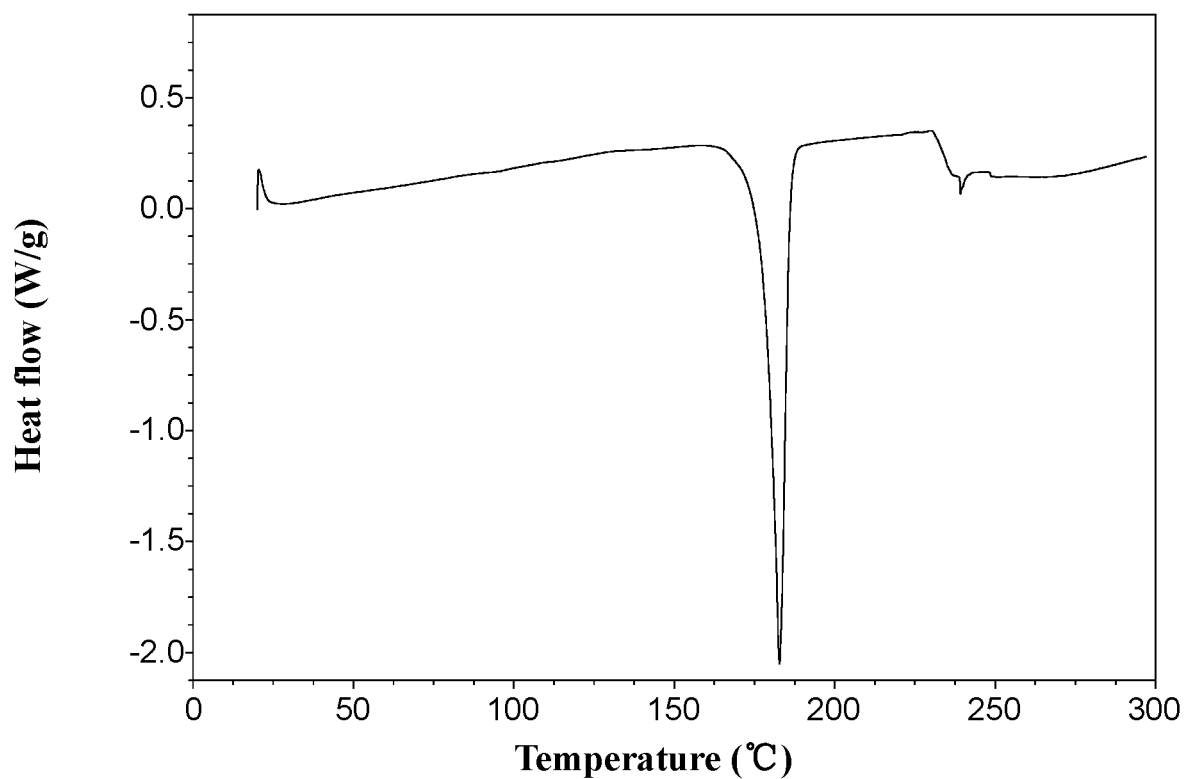
FIG. 17 is the DSC thermogram of ODM-201 Form 5 in the present invention.
Figure 18:
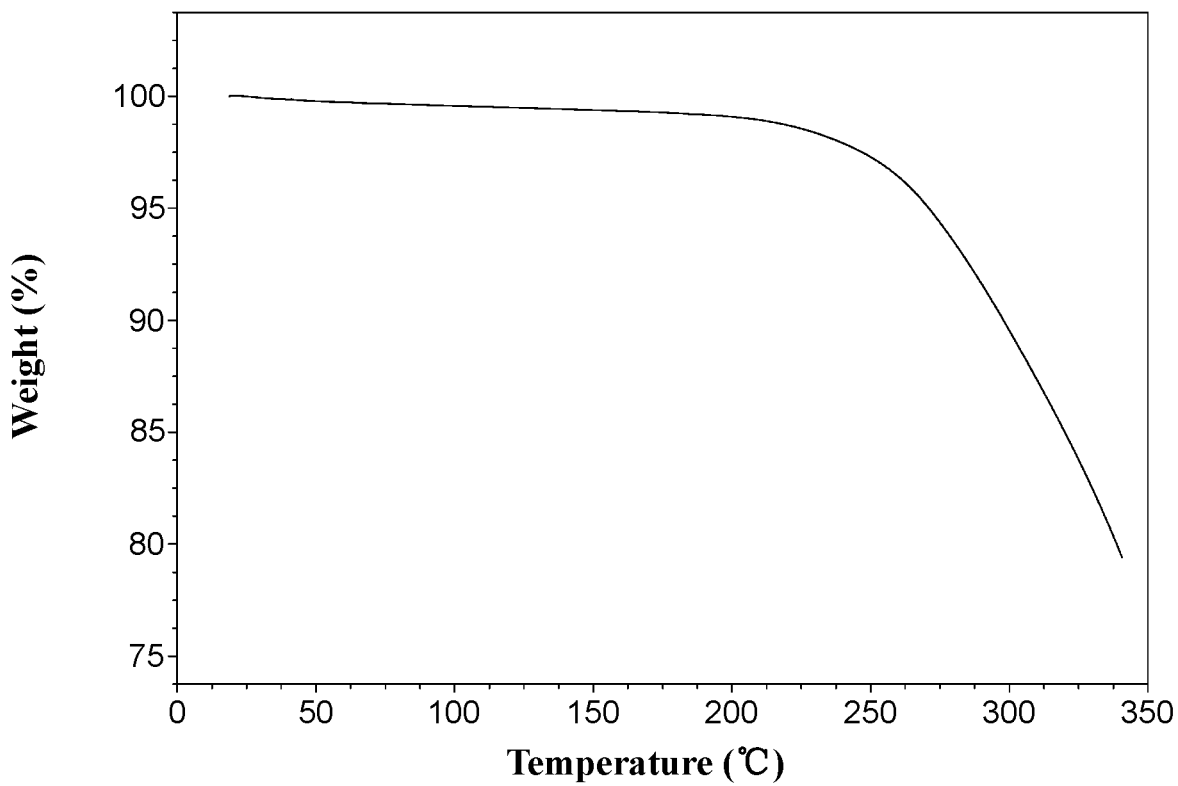
FIG. 18 is the TGA thermogram of ODM-201 Form 5 in the present invention.
Figure 19:
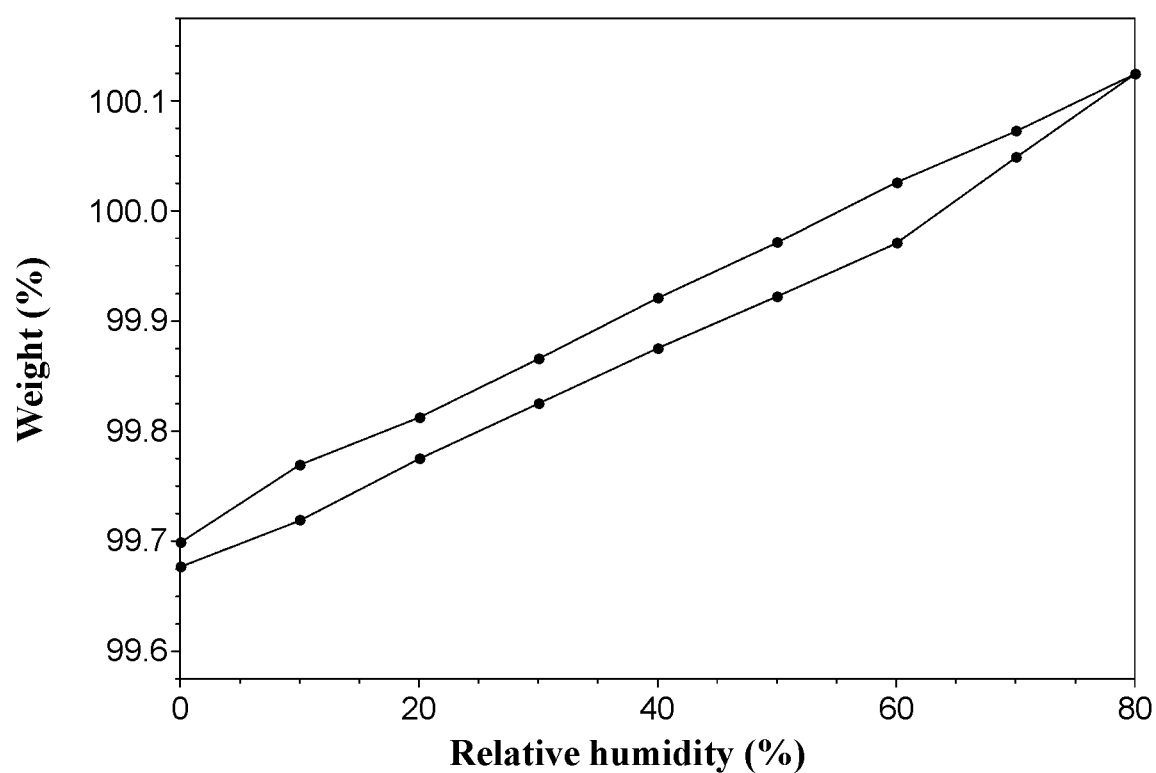
FIG. 19 is the isothermal sorption curve of ODM-201 Form 5 in the present invention.

Its XRPD pattern is shown in FIG. 16.
Its DSC thermogram is shown in FIG. 17.
Its TGA thermogram is shown in FIG. 18.
Its isothermal sorption curve is shown in FIG. 19.

Example 26

Butanone (30.0 mL) was added to ODM-201 (150 mg) at 40° C. to form a solution, cooled to 4° C. at a cooling rate of 5° C./hour and let stand for crystallization for 5 days, filtered, and dried under vacuum at 130° C. for 1 hour to obtain ODM-201 Form 5 (128 mg).

Example 27

Acetone (3.0 mL) was added to ODM-201 (150 mg) at 60° C. to form a suspension, and filtered. The filtrate was cooled to 4° C. at a cooling rate of 10° C./hour and let stand for crystallization for 1 day, filtered, and dried under vacuum at 150° C. for 0.5 hour to obtain ODM-201 Form 5 (132 mg).

Example 28

Acetone (9.0 mL) was added to ODM-201 (150 mg) at 53° C. to form a solution, cooled to 4° C. at a cooling rate of 10° C./hour and let stand for crystallization for 2 days, filtered, and dried under vacuum at 160° C. for 0.8 hour to obtain ODM-201 Form 5 (118 mg).

Example 29

Acetone (15.0 mL) was added to ODM-201 (150 mg) at 45° C. to form a solution, cooled to 4° C. at a cooling rate of 5° C./hour and let stand for crystallization for 3 days, filtered, and dried under vacuum at 160° C. for 0.8 hour to obtain ODM-201 Form 5 (107 mg).

The samples prepared in Examples 26 to 29 had the same or similar XRPD pattern (not shown), DSC thermogram (not shown) and TGA thermogram (not shown) as the sample in Example 25, indicating that the samples in Examples 26 to 29 and the sample in Example 25 have the same crystalline form.

Example 30

| Component | Dosage (mg) |
| --- | --- |
| ODM-201 Form 1 or ODM-201 Form 2 or ODM-201 Form 4 or ODM-201 Form 5 | 150 |
| starch | 180 |
| magnesium stearate | 5 |
| total | 340 |

ODM-201 Form 1 or ODM-201 Form 2 or ODM-201 Form 4 or ODM-201 Form 5 was blended with starch and magnesium stearate, and then filled into the capsule.

Example 31

| Component | Dosage (mg) |
| --- | --- |
| ODM-201 Form 1 or ODM-201 Form 2 or ODM-201 Form 4 or ODM-201 Form 5 | 100 |
| microcrystalline cellulose | 125 |
| silica colloid | 10 |
| stearic acid | 5 |
| total | 240 |

ODM-201 Form 1 or ODM-201 Form 2 or ODM-201 Form 4 or ODM-201 Form 5 was blended with microcrystalline cellulose, silica colloid and stearic acid, and then compressed into tablets.

Comparative Example 1

Crystalline form stability experiment: 15 mg of amorphous ODM-201, ODM-201 Form 1, ODM-201 Form 2, ODM-201 Form 4 and ODM-201 Form 5 in the present invention were respectively placed under the following different conditions: high temperature 60° C., high moisture content 97% RH, and 40° C.-75% RH. The samples were stored for 7 days before analyzed by XRD crystalline form measurements.

| Forms | The test results after 7 days |
| --- | --- |
| amorphous ODM-201 | Amorphous with weak crystalline peaks |
| ODM-201 Form 1 | Form 1 |
| ODM-201 Form 2 | Form 2 |
| ODM-201 Form 4 | Form 4 |
| ODM-201 Form 5 | Form 5 |

The results show that: ODM-201 Form 1, ODM-201 Form 2, ODM-201 Form 4, and ODM-201 Form 5 of the present invention kept their original crystalline forms after having been stored for 7 days under the conditions of high temperature 60° C., high moisture content 97% RH, and 40° C.-75% RH. The ODM-201 amorphous form began to show a weak crystalline state after having been stored for 7 days under the conditions of high temperature 60° C., high moisture content 97% RH, and 40° C.-75% RH. It indicated that ODM-201 Form 1, ODM-201 Form 2, ODM-201 Form 4 and ODM-201 Form 5 of the present invention have better crystal stability.

Comparative Example 2

Chemical stability experiment: 20 mg of amorphous ODM-201, ODM-201 Form 1, ODM-201 Form2, ODM-201 Form 4 and ODM-201 Form 5 in the present invention were respectively placed under dry condition at 60° C. for 7 days. Then the samples were analyzed by HPLC purity measurements, and the results are shown in the table below.

| | Purity (%) | |
| --- | --- | --- |
| ODM-201 | 1 day | 7 days |
| Amorphous | 99.7 | 98.2 |
| Form 1 | 99.7 | 99.6 |
| Form 2 | 99.6 | 99.6 |
| Form 4 | 99.2 | 99.1 |
| Form 5 | 99.6 | 99.5 |

The results show that: after having been stored for 7 days, the chemical purity of amorphous ODM-201 reduced by more than 1%. ODM-201 Form 1, ODM-201 Form 2, ODM-201 Form 4 and ODM-201 Form 5 of the present invention still kept their original respective purity level. The results indicate that compared to the prior art, ODM-201 Form 1, ODM-201 Form 2, ODM-201 Form 4 and ODM-201 Form 5 have better chemical stability.

Comparative Example 3

ODM-201 Form 1, ODM-201 Form 2, ODM-201 Form 3, ODM-201 Form 4 and ODM-201 Form 5 in the present invention were tested for the apparent water solubility, and the specific operations were as follows.

Weighed accurately and placed 15 mg of sample in a 20 mL glass vial containing 5 mL of water, and placed the vials at 25±2° C. and 37±2° C. water bath respectively, stirred in dark (about 200 rpm/min) for 1 hour, filtered with a 0.45 m filter and took the supernatant, diluted to a certain concentration, analyzed the concentration by HPLC.

The results shown in the table below indicate that the water solubilities of ODM-201 Form 1, ODM-201 Form 2, ODM-201 Form 3, ODM-201 Form 4 and ODM-201 Form 5 in the present invention are: ODM-201 Form 4>ODM-201 Form 2>ODM-201 Form 5>ODM-201 Form 3>ODM-201 Form 1.

| Forms | Solubility (μg/mL) | |
|---|---|---|
| | 25 ± 2° C. | 37 ± 2° C. |
| ODM-201 Form 1 | 9.9 | 17.4 |
| ODM-201 Form 2 | 27.6 | 54.8 |
| ODM-201 Form 3 | 12.5 | 24.3 |
| ODM-201 Form 4 | 59.5 | 88.6 |
| ODM-201 Form 5 | 17.7 | 29.5 |

All of the patents, patent application publications, patent applications and non-patent publications cited in this specification are incorporated into this application by reference in their entireties.

The described above are only specific aspects for illustrating the present invention, but without limiting it to that. Any changes or alternations, without creative work, made by those skilled in the art within the technical scope disclosed by the present invention, should fall within the scope of the present invention. Therefore, the scope of protection of the present invention shall be subject to the scope of protection defined in the claims.

What is claimed is:

1. Form 4 of N-1-(3-(3-chloro-4-cyanophenyl)-1H-pyrazol-1-yl)prop-2-yl)-5-(1-hydroxylethyl)-1H-pyrazole-3-carboxamide (ODM -201), wherein, measured using Cu-Kα radiation, the X-ray powder diffraction pattern of the ODM -201 Form 4, expressed as 2θ angles, comprises the following characteristic peaks: 7.8° ±0.2°, 9.2° ±0.2°, 11.2° ±0.2° and 14.5° ±0.2°.

2. The ODM-201 Form 4 according to claim 1, wherein the X-ray powder diffraction pattern of the ODM-201 Form 4, expressed as 2θ angles, further comprises the following characteristic peaks: 15.5° ±0.2°, 16.8° ±0.2° and 22.3° ±0.2°.

3. The ODM-201 Form 4 according to claim 2, wherein the X-ray powder diffraction pattern of the ODM-201 Form 4, expressed as 2θ angles, further comprises the following characteristic peaks: 18.4° ±0.2°, 20.2° ±0.2° and 23.5° ±0.2°.

4. A method of preparing the ODM-201 Form 4 according to claim 1, the method comprising:
forming a solution of ODM-201 in a mixed solvent of water and an organic solvent at 50-60° C.,
filtering the solution, cooling slowly and letting the solution stand for crystallization, separating precipitated crystals, and drying to obtain the ODM-201 Form 4; wherein:
the organic solvent is trifluoroethanol, a ketone, or a mixture thereof;
the mass-volume ratio of ODM-201 to the solvent is from 30 to 68 mg:1 mL;
the cooling rate is from 5 to 10° C/hour;
the duration for crystallization is from 1 to 15 days, and the crystallization temperature is 4° C.;
the drying temperature is room temperature; and
the duration for drying is 1 to 12 hours.

5. Form 5 of N-((s)-1-(3-(3-chloro-4-cyanophenyl)-1H-pyrazol-1-yl)prop-2-yl)-5-(1-hydroxylethyl)-1H-pyrazole-3-carboxamide (ODM -201), wherein, measured using Cu-Kα radiation, the X-ray powder diffraction pattern of the ODM -201 Form 5, expressed as 2θ angles, comprises the following characteristic peaks: 9.2° ±0.2°, 13.6° ±0.2°, 14.4° ±0.2°, 14.6° ±0.2°, 15.5° ±0.2° and 16.8° ±0.2°.

6. The ODM-201 Form 5 according to claim 5, wherein the X-ray powder diffraction pattern of the ODM-201 Form 5, expressed as 2θ angles, further comprises the following characteristic peaks: 11.5° ±0.2°, 18.4° ±0.2°, 19.1° ±0.2°, 20.4° ±0.2°, 23.3° ±0.2°, 24.2° ±0.2° and 25.2° ±0.2°.

7. The ODM-201 Form 5 according to claim 6, wherein the X-ray powder diffraction pattern of the ODM-201 Form 5, expressed as 2θ angles, further comprises the following characteristic peaks: 16.1° ±0.2°, 17.7° ±0.2°, 22.1° ±0.2°, 22.5° ±0.2° and 27.4° ±0.2°.

8. A method of preparing the ODM-201 Form 5 according to claim 5, the method comprising:
forming a solution of ODM-201 in a solvent at 40-60° C., cooling slowly and letting the solution stand for crystallization, separating precipitated crystals, and drying at high temperature to obtain the ODM -201 Form 5; wherein:
the solvent is a $C_3$ to $C_4$ ketone;
the mass-volume ratio of ODM-201 to the solvent is from 5 to 50 mg:1 mL;
the cooling rate is from 5 to 10° C/hour;
the duration for crystallization is from 1 to 5 days, and the crystallization temperature is 4° C.;
the drying temperature is 115 to 160° C.; and
the duration for drying is 0.5 to 1 hour.

9. A pharmaceutical composition, comprising a therapeutically effective amount of the ODM-201 Form 4 according to claim 1, and at least one pharmaceutically acceptable carrier or adjuvant.

10. The pharmaceutical composition according to claim 9, wherein the pharmaceutical composition is in the form of an oral formulation selected from the group consisting of a tablet, a capsule, a granule, an emulsion, a suspension, and a solution.

11. A method for reducing the severity of prostate cancer in a patient, wherein the method comprises administering to the patient in need thereof the pharmaceutical composition according to claim 9.

12. The method according to claim 4, wherein the organic solvent is trifluoroethanol.

13. The method according to claim 4, wherein the volume percentage of water in the mixed solvent is 10 to 60%.

14. The method according to claim 8, wherein the solvent is acetone.

15. The method according to claim 8, wherein the drying temperature is 120 to 150° C.

16. A pharmaceutical composition, comprising a therapeutically effective amount of the ODM-201 Form 5 according to claim 5, and at least one pharmaceutically acceptable carrier or adjuvant.

17. The pharmaceutical composition according to claim 16, wherein the pharmaceutical composition is in the form of an oral formulation selected from the group consisting of a tablet, a capsule, a granule, an emulsion, a suspension, and a solution.

18. A method for reducing the severity of prostate cancer in a patient, wherein the method comprises administering to the patient in need thereof the pharmaceutical composition according to claim 16.

19. The method according to claim 11, wherein the pharmaceutical composition comprises about 100-700 mg of the ODM-201 Form 4.

20. The method according to claim 18, wherein the pharmaceutical composition comprises about 100-700 mg of the ODM-201 Form 5.

\* \* \* \* \*

UNITED STATES PATENT AND TRADEMARK OFFICE
CERTIFICATE OF CORRECTION

PATENT NO. : 11,236,073 B2
APPLICATION NO. : 16/637465
DATED : February 1, 2022
INVENTOR(S) : Xiaohong Sheng and Xiaoxia Sheng Page 1 of 1

It is certified that error appears in the above-identified patent and that said Letters Patent is hereby corrected as shown below:

In the Claims

In Column 19, Claim 1, Line 31, delete "N-1" and insert -- N-((s)-1 --, therefor.

Signed and Sealed this
Fifth Day of March, 2024

Katherine Kelly Vidal
*Director of the United States Patent and Trademark Office*